(12) United States Patent
Maurer et al.

(10) Patent No.: US 9,259,219 B2
(45) Date of Patent: *Feb. 16, 2016

(54) SURGICAL NEEDLE COATINGS AND METHODS

(75) Inventors: Robert Maurer, Somerset, NJ (US); S. Neil Bar, Somerset, NJ (US); Eric Hinrichs, Bucks, PA (US); Michael Hamilton, Somerset, NJ (US); Thomas Wilkes, New Brunswick, NJ (US)

(73) Assignee: Ethicon, LLC, San Lorenzo, PR (US)

( * ) Notice: Subject to any disclaimer, the term of this patent is extended or adjusted under 35 U.S.C. 154(b) by 315 days.

This patent is subject to a terminal disclaimer.

(21) Appl. No.: 12/858,481

(22) Filed: Aug. 18, 2010

(65) Prior Publication Data

US 2011/0112565 A1    May 12, 2011

Related U.S. Application Data

(63) Continuation-in-part of application No. 12/614,665, filed on Nov. 9, 2009, now abandoned, and a continuation-in-part of application No. 12/614,669, filed on Nov. 9, 2009, now abandoned.

(51) Int. Cl.
| | |
|---|---|
| *B05D 5/00* | (2006.01) |
| *B05D 3/02* | (2006.01) |
| *B05D 7/00* | (2006.01) |
| *A61B 17/06* | (2006.01) |
| *C09D 183/04* | (2006.01) |
| *A61B 17/00* | (2006.01) |

(Continued)

(52) U.S. Cl.
CPC ........ *A61B 17/06066* (2013.01); *C09D 183/04* (2013.01); *A61B 2017/00526* (2013.01); *C08G 77/16* (2013.01); *C08G 77/20* (2013.01)

(58) Field of Classification Search
CPC .................................. B05D 7/00; B05D 3/02
USPC .......................................... 427/2.28; 606/185
See application file for complete search history.

(56) References Cited

U.S. PATENT DOCUMENTS

| 1,944,823 A | 1/1934 | Lamont |
|---|---|---|
| 4,256,870 A | 3/1981 | Eckberg |

(Continued)

FOREIGN PATENT DOCUMENTS

| JP | 2005306902 | 11/2005 |
|---|---|---|
| WO | WO 9832474 | 7/1998 |
| WO | WO 2007024270 | 3/2007 |

OTHER PUBLICATIONS

Petroleum ether, Sigma-Aldrich.*

(Continued)

*Primary Examiner* — Dah-Wei D Yuan
*Assistant Examiner* — Hai Yan Zhang
(74) *Attorney, Agent, or Firm* — Mintz Levin/Boston Office

(57) ABSTRACT

The present invention provides novel medical devices for use in surgical procedures and methods for manufacturing novel medical devices. In some embodiments, the novel medical devices can include surgical needles that are capable of being repeatedly passed through tissue using minimal force. More particularly, the surgical needles can be manufactured with one or more coatings that provide the surgical needles with both durability and lubricity for ease of repeated and successive passes through tissue. Novel methods for manufacturing the surgical needles and for providing and applying coatings to the surgical needles are also provided.

10 Claims, 12 Drawing Sheets

(51) Int. Cl.
*C08G 77/16* (2006.01)
*C08G 77/20* (2006.01)

(56) References Cited

U.S. PATENT DOCUMENTS

| | | | |
|---|---|---|---|
| 4,720,521 A * | 1/1988 | Spielvogel et al. | 524/862 |
| 4,806,430 A * | 2/1989 | Spielvogel | A61L 29/085 |
| | | | 206/571 |
| 5,258,013 A | 11/1993 | Granger et al. | |
| 5,458,616 A | 10/1995 | Granger et al. | |
| 5,463,010 A | 10/1995 | Hu et al. | |
| 5,536,582 A | 7/1996 | Prasad et al. | |
| 5,645,884 A | 7/1997 | Harlow, Jr. et al. | |
| 5,688,598 A * | 11/1997 | Keck et al. | C08G 18/698 |
| | | | 428/421 |
| 5,911,711 A | 6/1999 | Pelkey | |
| 5,985,355 A * | 11/1999 | Walther et al. | A61L 31/10 |
| | | | 427/2.28 |
| 5,997,517 A | 12/1999 | Whitbourne | |
| 6,018,860 A | 2/2000 | Smith et al. | |
| 6,231,990 B1 * | 5/2001 | Lin et al. | 428/447 |
| 6,265,016 B1 | 7/2001 | Hostettler et al. | |
| 6,306,176 B1 | 10/2001 | Whitbourne | |
| 6,325,853 B1 | 12/2001 | Hogan et al. | |
| 6,335,383 B1 * | 1/2002 | Scopelianos et al. | 523/105 |
| 6,558,409 B1 * | 5/2003 | Roby | 606/222 |
| 6,656,167 B2 | 12/2003 | Numao et al. | |
| 6,936,297 B2 | 8/2005 | Roby et al. | |
| 7,015,262 B2 | 3/2006 | Leong | |
| 7,028,867 B2 | 4/2006 | Acum et al. | |
| 7,354,628 B2 | 4/2008 | Steube | |
| 2004/0040467 A1 | 3/2004 | Thomas et al. | |
| 2004/0071988 A1 | 4/2004 | Nawrocki et al. | |
| 2004/0086542 A1 | 5/2004 | Hossainy et al. | |
| 2004/0172120 A1 * | 9/2004 | Cheng et al. | A61L 31/10 |
| | | | 623/1.11 |
| 2004/0258931 A1 | 12/2004 | Zamora et al. | |
| 2004/0260269 A1 * | 12/2004 | Assaf | 604/506 |
| 2004/0266302 A1 * | 12/2004 | DiSalvo et al. | 442/382 |
| 2005/0064088 A1 | 3/2005 | Fredrickson | |
| 2005/0158470 A1 | 7/2005 | Maiorino | |
| 2005/0226993 A1 | 10/2005 | Nawrocki et al. | |
| 2005/0240223 A1 | 10/2005 | Roby et al. | |
| 2005/0255249 A1 | 11/2005 | Schlatterbeck et al. | |
| 2006/0190040 A1 | 8/2006 | Roby | |
| 2006/0224237 A1 | 10/2006 | Furst et al. | |
| 2007/0128343 A1 | 6/2007 | Chappa | |
| 2007/0149629 A1 | 6/2007 | Donovan et al. | |
| 2007/0254091 A1 | 11/2007 | Fredrickson et al. | |
| 2007/0267464 A1 | 11/2007 | Vitcak et al. | |
| 2007/0299402 A1 * | 12/2007 | Ishii et al. | 604/164.13 |
| 2008/0071228 A1 * | 3/2008 | Wu et al. | 604/234 |
| 2008/0102192 A1 * | 5/2008 | Johnson et al. | 427/2.1 |
| 2008/0139683 A1 | 6/2008 | Flynn et al. | |
| 2008/0147117 A1 * | 6/2008 | Cichocki | A61B 17/06066 |
| | | | 606/223 |
| 2008/0277448 A1 | 11/2008 | Roby et al. | |
| 2009/0026291 A1 | 1/2009 | Shimada | |
| 2009/0148496 A1 * | 6/2009 | Schmitz et al. | A61L 31/10 |
| | | | 424/426 |
| 2011/0111116 A1 | 5/2011 | Maurer et al. | |
| 2011/0112566 A1 | 5/2011 | Maurer et al. | |
| 2013/0189422 A1 | 7/2013 | Maurer et al. | |
| 2013/0209664 A1 | 8/2013 | Maurer et al. | |

OTHER PUBLICATIONS

3M Material Safety Data Sheet for HFE-72DE.
Momentive® Performance Materials Product Description for Product Code Nos. SS4004P, SS4044P, SS4120, SS4155, and SS4179.
Momentive® Performance Materials Safety Data Sheet for Product Code No. SS4044P.
NuSil® Technologies MED-4162 Product Profile.
NuSil® Technologies Material Safety Data Sheet for DSP-9769.
International Search Report, PCT/US2010/53541, dated Dec. 28, 2010.
International Search Report, PCT/US2010/53552, dated Dec. 21, 2010.
International Search Report, PCT/US2010/53552, dated Jan. 3, 2010.
U.S. Appl. No. 12/614,665 for "Surgical Needle Coating and Methods" filed Nov. 9, 2009.
International Preliminary Report on Patentability mailed May 24, 2012 for Application No. PCT/US2011/053541 (7 Pages).
International Preliminary Report on Patentability mailed May 24, 2012 for Application No. PCT/US2010/053545 (8 Pages).
International Preliminary Report on Patentability for Application No. PCT/US2010/053552 mailed May 24, 2012. (8 pages).

* cited by examiner

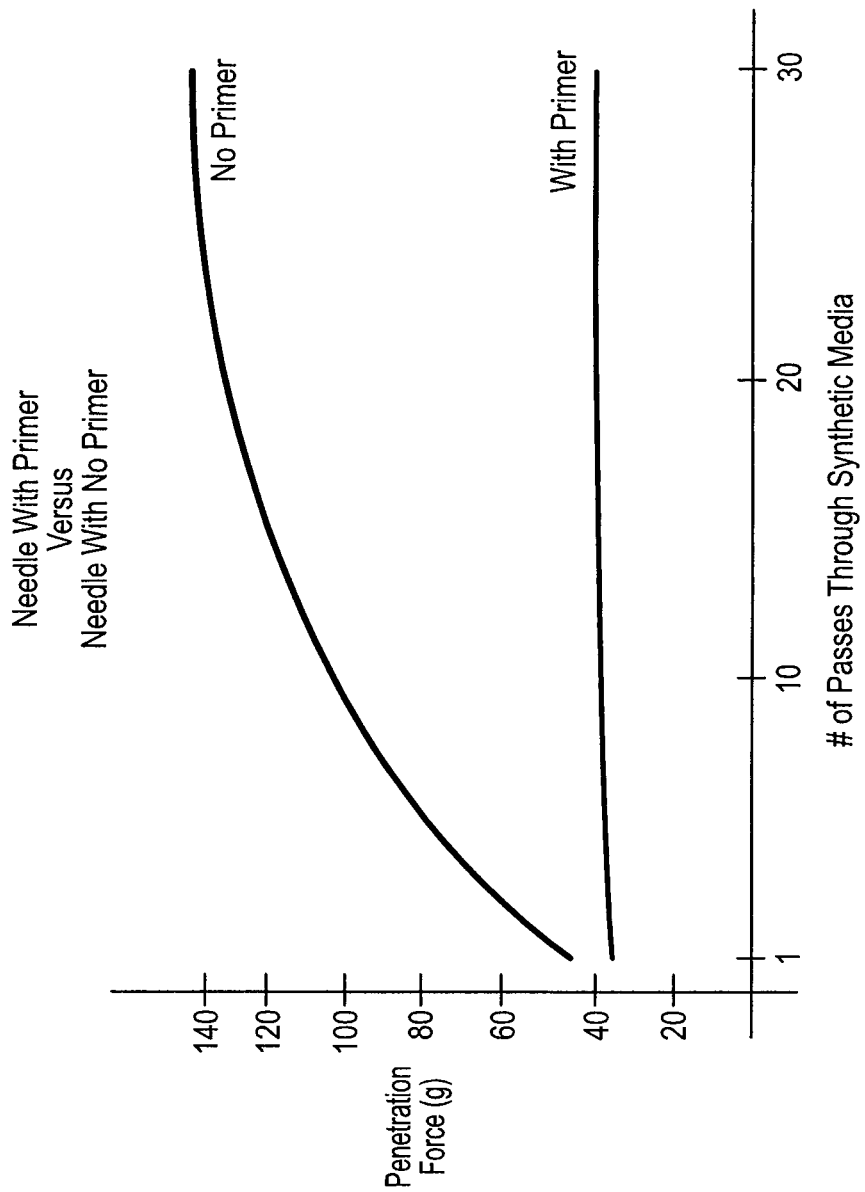

Spray Coating Versus Dip Coating

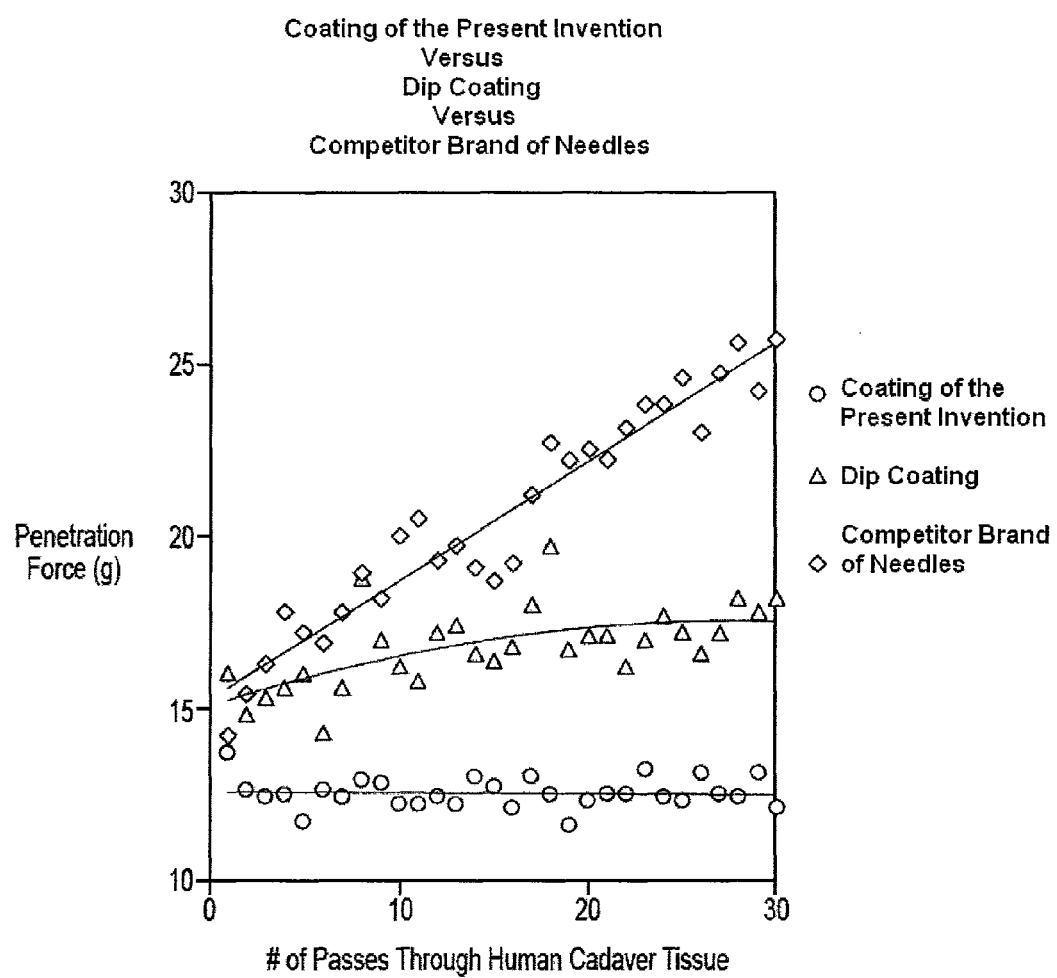

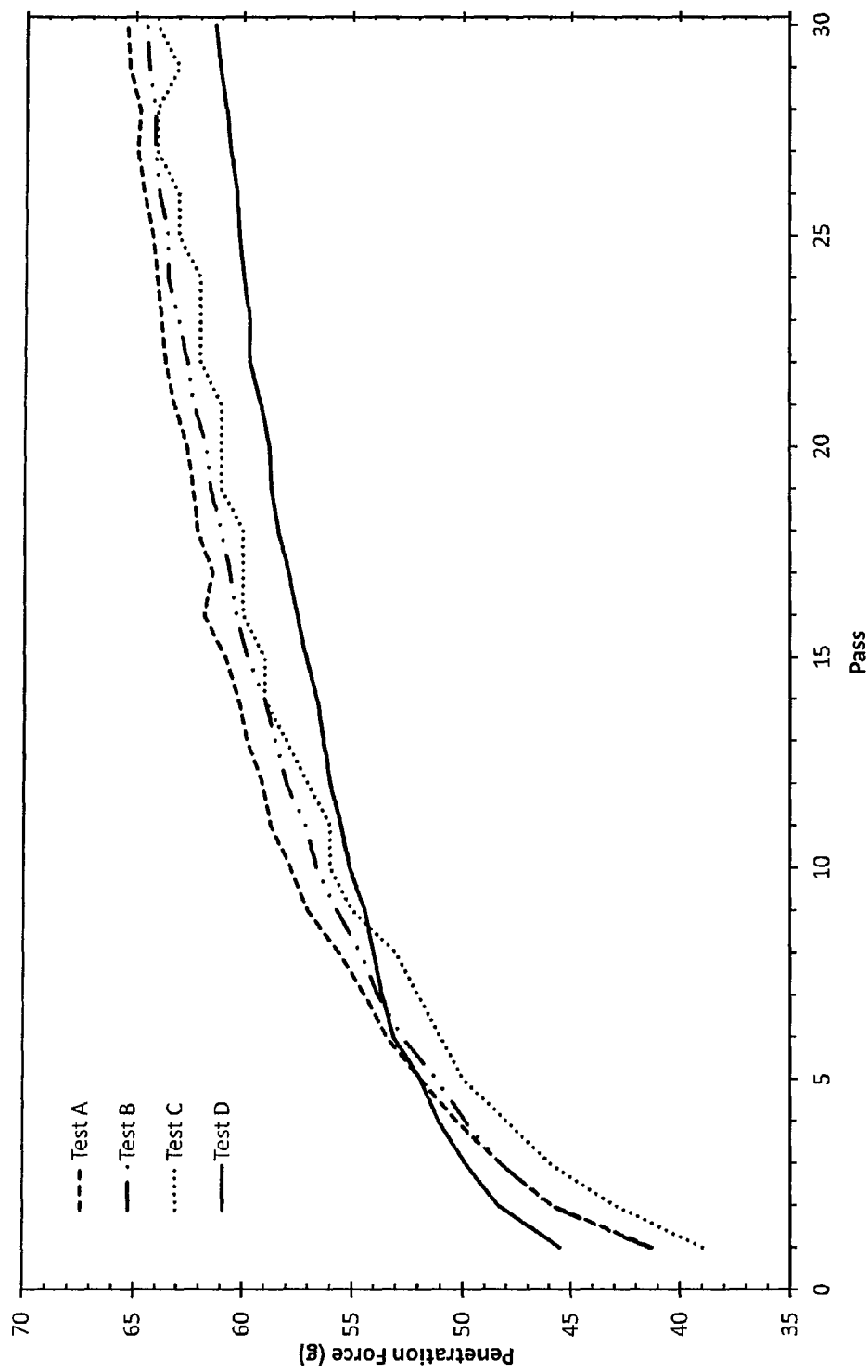

SURGICAL NEEDLE COATINGS AND METHODS

REFERENCE TO RELATED APPLICATIONS

This application is a continuation-in-part of U.S. patent application Ser. No. 12/614,669, filed on Nov. 9, 2009 and entitled "Surgical Needle Coatings and Methods" and U.S. patent application Ser. No. 12/614,665, filed on Nov. 9, 2009 and entitled "Surgical Needle Coatings and Methods," both of which are hereby incorporated by reference in their entireties.

FIELD OF THE INVENTION

The present invention relates to coated medical devices and methods for manufacturing the same.

BACKGROUND OF THE INVENTION

Coated medical devices which repeatedly come into contact with bodily tissue, such as surgical needles, are required to be lubricious, yet durable enough to withstand multiple contacts with tissue. However, lubricity is often sacrificed at the expense of making a more durable coating that adheres well to medical devices. There are many coating materials that are extremely lubricious, but either do not adhere well to the desired substrates or easily wear off the substrate during use. Likewise, many extremely durable coatings exist, but these coatings are not considered lubricious. Various attempts have been made to find coating compositions and/or a method of applying coating compositions that can provide durability and lubricity simultaneously. Accordingly, the present invention solves this problem by providing coating compositions and methods of application, which provide both durability and lubricity, as well as decreased manufacturing time.

SUMMARY OF THE INVENTION

The present invention provides methods and devices for providing a durable and lubricious body, structure, and/or medical device. In one exemplary embodiment, a method for coating a body, structure, and/or medical device is provided and can include providing a medical device and applying a single, homogenous coating to at least a portion of a surface of the medical device with a thickness in the range of about 1 micron to about 12 microns. While the single, homogeneous coating can have many components, in some embodiments, the single, homogeneous coating can include a vinyl functionalized organopolysiloxane and a polydimethylsiloxane. Applying a single, homogeneous coating to a surface of the medical device can include applying a coating with a thickness in the range of about 1 micron to about 3.5 microns. In one embodiment, the surface of the medical device can include a primer that includes a silicone. The single, homogeneous coating can be sprayed onto a surface of the medical device. The surface can be an exterior surface, an interior surface, or some combination of exterior and interior surfaces. In some embodiments, the single, homogeneous coating can be cured on the surface of the medical device for a time in the range of about 10 seconds to about 30 seconds.

The medical device can be formed of any suitable material known in the art, including tungsten alloys, refractory alloys, stainless steels, nitinol, and tantalum. The tungsten alloy can be, for example, tungsten-rhenium. In some embodiments, applying a single, homogeneous coating can include delivering the single, homogeneous coating to the surface of the medical device in a high vapor pressure, low boiling point solvent. The high vapor pressure, low boiling point solvent can be, for example, a hydrofluoroether solvent. The single, homogeneous coating can be applied to any medical device known in the art, and in some embodiments, the method can include providing an elongate medical device having a tissue penetrating portion.

In other aspects, devices are provided, and in one exemplary embodiment, a coated device is provided and can include a substrate, wherein at least a portion of the substrate is coated with a coating comprising a vinyl functionalized organopolysiloxane and a polydimethylsiloxane. The coating can be a single layer having a thickness in the range of about 1 micron to about 3.5 microns. In some embodiments, the coating can be configured to be delivered to the substrate in a high vapor pressure, low boiling point solvent such that the body exhibits substantially constant penetration over thirty passes of the body through tissue. The device can be formed from any suitable material known in the art, including tungsten alloys, refractory alloys, stainless steels, nitinol, and tantalum. In some embodiments, the substrate can be a medical device. Further, the coating includes vinyl functionalized organopolysiloxane in the range of about 10 wt. % to about 90 wt. % and polydimethylsiloxane in the range of about 10 wt. % to about 90 wt. %. The vinyl functionalized organopolysiloxane can be for example, Momentive® Product Code No. MSC2631 silicone manufactured by Momentive® Performance Materials of Waterford, N.Y.

In another aspect, a medical device is provided and can include a structure and/or body and a single, homogeneous coating comprising a lubricious silicone disposed on a surface, e.g., an exterior and/or interior surface of the body. The body can exhibit, for example, substantially constant penetration over thirty passes of the body through tissue. In some embodiments, the single, homogeneous coating can be formed of a vinyl functionalized organopolysiloxane and a polydimethylsiloxane. The body can have many configurations known in the art, and can include an elongate body having a tissue penetrating portion. In addition, the medical device can be an assembly including a plurality of components and/or operating parts, and the body can be one of the plurality of components and/or operating parts. One or more, and in some cases all, of the plurality of components and/or operating parts can be coated with the single, homogenous coating.

In some embodiments, the single, homogeneous coating can be configured to be cured at a temperature of about 200 degrees Celsius using infrared radiation having a wavelength in a range of about 1.4 µm to about 3.0 µm. The single, homogeneous coating can also be configured to be cured for a time in the range of about 1 second to about 60 seconds and/or for a time in the range of about 10 seconds to about 30 seconds. In other embodiments, the single, homogeneous coating can be configured to be cured on the surface of the body in a convection oven for a time in the range of about 1 hour to about 5 hours at a temperature of about 60 degrees Celsius to about 180 degrees Celsius and/or for a time in the range of about 2.5 hours to about 3.5 hours at a temperature of about 100 degrees Celsius to about 140 degrees Celsius.

In still further aspects, methods for coating a medical device are provided and can include providing a lubricious silicone coating comprising a solvent having a boiling point less than about 43 degrees Celsius. The method can also include applying the lubricious silicone coating to the medical device and curing the lubricious silicone coating for a time in the range of about 1 second to about 60 seconds. The solvent can have a vapor pressure of, for example, about 350 mm Hg. Further, curing the lubricious silicone coating can include curing the coating at a temperature of about 200 degrees Celsius for a time in the range of about 10 seconds to about 30 seconds using infrared radiation having a wavelength in the range of about 1.4 µm to about 3.0 µm. While the lubricious silicone coating can be formed of many compositions, in one embodiment, the lubricious silicone coating can include a single, homogeneous layer of a vinyl functionalized organopolysiloxane and a polydimethylsiloxane.

The invention will be more fully understood from the following detailed description taken in conjunction with the accompanying drawings, in which:

BRIEF DESCRIPTION OF THE DRAWINGS

FIG. 5 is a graphical representation comparing the force required to pass primed and unprimed surgical needles through synthetic media;

FIG. 9 is a graphical representation comparing the forces associated with passing three different coating compositions and application methods through human cadaver tissue; and FIG. 10 is a graphical representation comparing the forces associated with passing needles coating with a single, homogeneous coating and needles coated with two coatings through synthetic media.

DETAILED DESCRIPTION OF THE INVENTION

Figure 1:
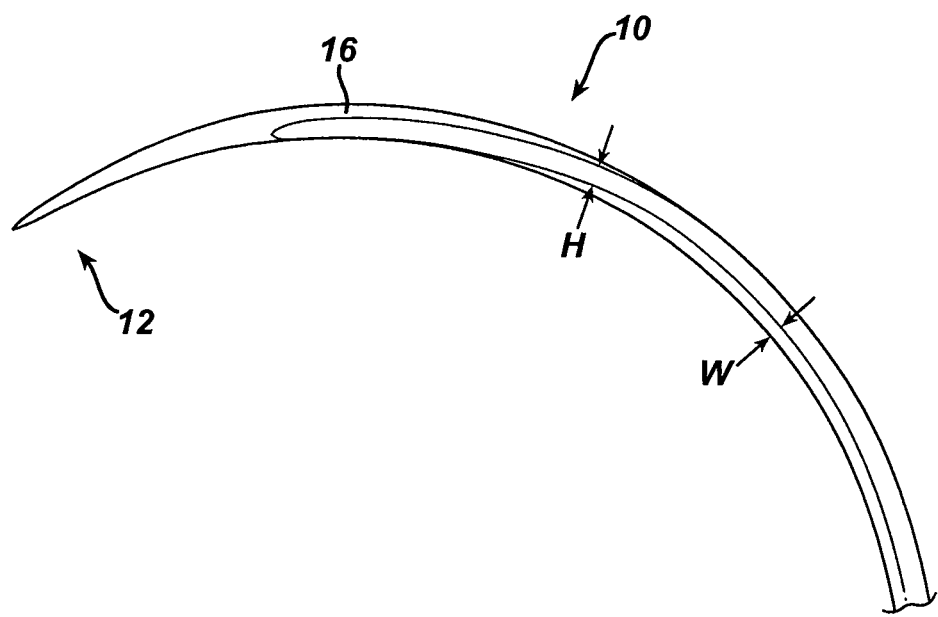
FIG. 1 is a perspective view of one exemplary embodiment of a surgical needle.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides novel medical devices for use in surgical procedures and methods for manufacturing novel medical devices. In some embodiments, the novel medical devices can include one or more bodies, one or more structures, and/or an assembly of components and/or operating parts. In one embodiment, the novel medical devices can include novel surgical needles that are capable of being repeatedly passed through tissue with ease of penetration. More particularly, the novel surgical needles can be manufactured with two or more different coats and/or coatings that provide the surgical needles with both durability and lubricity for ease of repeated and successive passes through tissue. Novel methods for manufacturing the surgical needles and for providing and applying durable coatings to the surgical needles are also provided. As they are used herein, the terms "coat" and "coating" are used interchangeably.

While many types of medical devices and surgical needles are contemplated, in one embodiment, a biocompatible surgical needle is provided having a single, homogeneous coating applied thereto such that the coating is both durable and lubricious. The single, homogeneous coating can be applied to an exterior and/or interior surface of a medical device, and can be applied to one or more portions of the exterior and/or interior surfaces. The single, homogenous coating can be a partial and/or discontinuous coating of the exterior and/or interior surface, or it can be applied to the entire exterior and/or interior surface. In another embodiment, two or more different coatings can be applied successively to the surgical needle. A base coating can be applied to the needle to provide durability for a different top coating that is applied to provide lubrication. The base coating can also be lubricious to enhance the lubricity of the top coating. In some embodiments, the single, homogeneous coating can crosslink with itself and/or the base and top coatings can interact, for example, by crosslinking or by one or more other bonding mechanism. Because of the bonding between the base coating and top coating, the base coating retains the top coating on the surgical needle. In this way, the base coating can assist in preventing the top coating from wearing and/or rubbing off after repeated passes through tissue. In other embodiments, each of the base coating and/or the top coating can crosslink with itself. The interaction between components within the single, homogeneous coating and/or between the durable base coating and the lubricious top coating assists in maintaining lubrication of the surgical needle so that it can consistently and repeatedly be passed through tissue with minimal force required.

Any number of coatings can be applied to the surgical needle depending on the surgical application and the composition of the surgical needle. For example, in another embodiment a primer coating can be applied to the surgical needle before the single, homogeneous coating and/or before the base and top coatings are applied. The primer coating can be different from the single, homogeneous coating or from the base and top coatings and it can bond with a surface of the surgical needle to provide an appropriate and secure surface on which to apply the base coating. In turn, the single, homogeneous coating and/or the base coating can bond to the primer coating such that the primer coating securely retains the single, homogeneous coating or the base coating on the surgical needle.

Novel methods for applying the coatings to various medical devices, such as surgical needles, are also provided. In some embodiments, a surgical needle can be spray coated with one or more coatings to provide the surgical needle with a uniform distribution thereof. For example, a spray coating machine having two spray nozzles directed toward one another can be provided for applying the single, homogeneous coating or for successively applying each top and base coating. One or more surgical needles can be passed between the two spray nozzles as they are spraying a coating. Such a configuration allows for uniform distribution of the coating on the surgical needle and minimizes the risk of pooling and/or dripping of the coating. Multiple coatings can be applied using this method, and prior to and/or after application of each coating, the surgical needle can be cured for a sufficient period of time effective to set and bond the coating (s). As will be discussed in more detail below, novel combinations of solvents and coating materials can allow for substantially reduced cure times when compared with techniques known in the art.

Exemplary surgical needles of the type contemplated herein can generally be used for any surgical procedures now known or yet to be developed. The surgical needles can be capable of penetrating and passing through any type of tissue, including any type of mammalian tissue including soft and hard tissues and tissues that have been calcified, and can be used to apply sutures to close an incision or wound, pass suture or other material through tissue, and/or simply create an opening in tissue. A person skilled in the art will appreciate the variety of uses for the surgical needles described herein.

Exemplary surgical needles can generally include an elongate member with a tissue penetrating tip on a distal end thereof for penetrating through tissue. The tissue penetrating tip can be pointed and can be as sharp or as dull as required for a particular surgical procedure. In some embodiments, the surgical needle can also include a suture attachment portion disposed on a proximal end of the elongate member for receiving and retaining suture. The surgical needle can have any geometry known in the art, including straight, taper point, taper cut, cutting edge, bayonet-shaped, curved, circular, etc. In addition, the surgical needle can have any cross-section including, but not limited to, round body, rectangular body, square body, ovular body, and I-beam. A person skilled in the art will appreciate the various combinations of shapes and cross-sections possible for a given needle.

Figure 2:
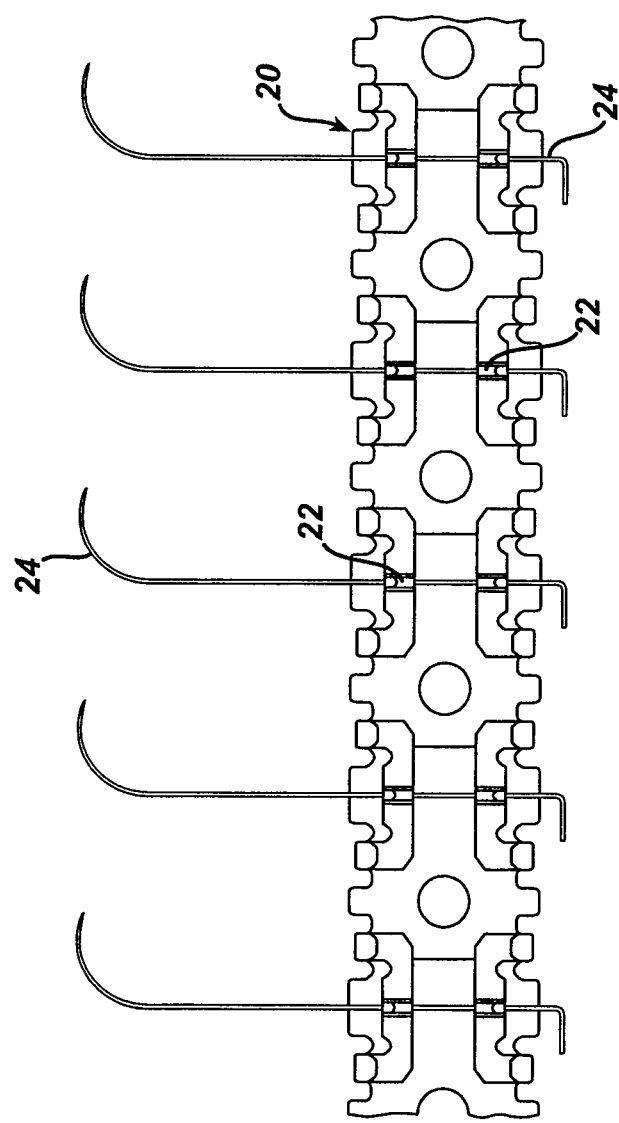
FIG. 2 is a side view of a carrier strip with surgical needles attached thereto for transporting the surgical needles.

In the manufacturing process, surgical needles can have a straightened and/or hook-shaped grasping portion to assist in applying coatings thereto. A conveyer mechanism and/or carrier strip for manufacturing a needle and/or moving a needle through a coating machine and/or curing mechanism can retain the needle for manufacturing, coating, and curing by attaching to the grasping portion. An exemplary carrier strip 20 for use with surgical needles 24 is illustrated in FIG. 2. The carrier strip 20 includes various latches 22 for retaining the curved surgical needles 24 thereon. This allows the surgical needles 24 to be moved using a conveyor style mechanism during the coating and/or curing process.

One exemplary embodiment of a surgical needle is illustrated in FIG. 1. As shown, a surgical needle 10 is provided having a curved elongate body 16 with a tissue penetrating tip 12 formed on a distal end thereof. The tip 12 has a circular cross-section and terminates in a sharp point for penetrating tissue. The curved elongate body 16 extends between the tip 12 and a suture attachment portion (not shown) and is in the form of an arc with a flattened, rectangular cross-section. While the surgical needle 10 can have any relative dimensions as needed, in the illustrated embodiment, a width W of the needle 10 is on the order of a height H of the needle 10. A suture attachment portion can have any form as needed for receiving and retaining suture.

Exemplary surgical needles can be formed of any suitable, biocompatible material known in the art. In some embodiments, a surgical needle can be made of a metallic alloy, including, but not limited to, titanium, stainless steels such as 420 stainless steel, 455 stainless steel, ETHALLOY® Needle Alloy, and 302 stainless steel, refractory alloys, nitinol, tantalum, as well as various other materials and alloys known in the art. In other embodiments, surgical needles can be made from a tungsten-rhenium alloy. Use of tungsten-rhenium alloy in making surgical needles can give the needles greater stiffness, strength, and ductility than the use of some other materials. Increased stiffness and strength properties allow the needle to be resistant to elastic deformation and to thus resist bending and springing when pushed through tough tissue, for example, calcified tissue. Increased ductility prevents the needle from breaking when bent or curved by a surgeon. Any of the needle alloy compositions can contain some percentage of any one or more of nickel, cobalt, chromium, molybdenum, tungsten, rhenium, niobium, etc. Exemplary needles and methods for manufacturing needles and carrier strips can be found in U.S. Pat. No. 6,018,860, entitled "Process for Manufacturing Drilled Taper Point Surgical Needles," which is hereby incorporated by reference in its entirety.

In some embodiments, two or more different coatings can be used to provide exemplary surgical needles with a durable lubricious surface for repeated passes through tissue. In one exemplary embodiment, a base coat can be used to coat an external surface of a surgical needle to provide durability to a top coat that is applied onto the base coat and that provides lubrication. The base coat preferably bonds with the top coat and thus prevents and/or lessens wear associated with repeated penetrations and passes through tissue. In some embodiments, a primer coat can optionally be applied prior to the base coat. The primer coat can bond with the surface of the surgical needle to provide a bonding surface for the base coat. The primer coat can add additional durability against wear for the base coat and top coat.

The base coat can include, for example, a silicone based composition characterized as a vinyl functionalized organopolysiloxane. The base coat solution includes a vinyl functionalized organopolysiloxane, polymethylhydrogen siloxane fluid crosslinking agent, and optionally a catalyst such as a conventional metal catalyst such as platinum or tin. The organopolysiloxane base polymer can be, for example, Momentive® Product Code No. MSC2631 silicone manufactured by Momentive® Performance Materials of Waterford, N.Y. Further information on the MSC2631 composition is available from the manufacturer's MSDS.

The base coat can be prepared using any high vapor pressure, low boiling point solvent known in the art. In some embodiments the solvent can be a hydrofluorether ("HFE") (e.g., HFE 72-DE solvent manufactured by 3M® of St. Paul, Minn.). The HFE solvent acts as a carrier for the silicone composition. It evaporates quickly from a composition under ambient conditions to limit migration of other substances in the composition and thus drastically reduces cure time of the composition. In addition, the HFE solvent leaves no residue after evaporation. It complies with health and safety regulations and is environmentally friendly. As will be appreciated by those skilled in the art, any suitable solvent can be used including, but not limited to, HFE, xylene, heptane, IsoPar K (Dow Corning), napthalene, toluene, and hydrofluorocarbons.

Additionally, a catalyst and a crosslinker can be added to the base coat. For example, Momentive® Product Code No. SS8010 platinum catalyst ("catalyst") and Momentive® Product Code No. SS4300 crosslinker ("crosslinker"), both manufactured by Momentive® Performance Materials of Waterford, N.Y., can be added during the preparation of the base coat to act as a crosslinker and catalyst. As will be appreciated by those skilled in the art, any suitable catalysts and crosslinkers can be used including, but not limited to, other crosslinkers containing a silicon-hydrogen moiety. Other catalysts may include conventional metal catalysts such as tin.

In preparing an exemplary base coat, 27.57 wt. % of the base silicone polymer, for example, a vinyl-functionalized organopolysiloxane, can be combined with 72.27 wt. % of the HFE solvent and mixed and/or agitated for an appropriate period of time, for example, for about five minutes. The catalyst can then be added to the mixture at 0.02 wt. % and the crosslinker can be added at 0.14 wt. %. The mixture can be agitated for another few minutes to ensure homogeneity, for example, about one to two more minutes. For an exemplary 48.43 g base coat sample, 13.35 g of the base silicone polymer can be combined with 35.00 g of the HFE solvent, 0.012 g of the catalyst, and 0.068 g of the crosslinker.

A top coat can be applied to a surgical needle. In some embodiments, the top coat can include a silicone based composition characterized as a hydroxyl terminated polydimethylsiloxane. The hydroxyl terminated polydimethylsiloxane generally includes dimethyl siloxane-hydroxy terminated, methylhydrogen siloxane, and trace amounts of several other siloxanes. The hydroxyl terminated polydimethylsiloxane can be, for example, NuSil® Technologies Silicone Product No. MED4162 manufactured by NuSil® Technologies of Carpentaria, Calif., which is a dispersion that contains 30% solids silicone in a 70% xylene solvent carrier.

The top coat can be prepared using a solvent, for example, the HFE solvent or any other compatible volatile-solvent. In preparing an exemplary top coat, 26 wt. % of the top silicone polymer can be combined with 74 wt. % of the HFE solvent. For example, for a 50 g top coat sample, 13.00 g of the top silicone polymer can be combined with 37.00 g of the HFE solvent.

In some embodiments, a primer coat can optionally be applied to a surgical device prior to applying the base coat. The primer coat can have any formulation capable of bonding to a surgical needle and capable of providing an appropriate substrate for applying a base coat. In one embodiment, the primer coat can be formed of, for example, polyalkylsiloxane and tetraethyl silicate. A polyalkylsiloxane and tetraethyl silicate primer coat can be formulated for coating difficult-to-bond substrates such as, for example, tungsten-rhenium alloys.

One example of a polyalkylsiloxane and tetraethyl silicate primer coat is Momentive® Product No. SS4044P ("SS4044P primer") manufactured by Momentive® Performance Materials of Waterford, N.Y. The SS4044P primer can include Momentive®) 10-30 wt. % of acetone, 1-5 wt. % of butanol, 10-30 wt. % of xylene isomers mixture, 5-10 wt. % of ethylbenzene, 10-30 wt. % of 2-propanol, 1-5 wt. % of tetraethyl silicate, and 10-30 wt. % of polyalkylsiloxane. Further information on the SS4044P primer composition is available from the manufacturer's MSDS.

In general, as noted above, the primer coat can covalently bond to the surgical needle to provide a substrate on which to apply other coatings. The base coat can be applied on top of the primer coat. As the top coat is applied over the base coat, the base coat will bond with the top coat to provide durability to the top coat. In essence, the bonding between the primer coat and the surgical needle anchors the other two coats to the needle surface. The bonding of the base coat to both the primer coat and the top coat anchors the top coat to the primer coat, and thus to the surgical needle surface, giving the top coat extended durability.

The coatings can generally be applied at any thickness as needed. The thickness of the individual coatings and the combined coatings should be sufficient to effectively provide the desired characteristics. For example, the primer coat can be applied to have a thickness in the range of about 0.01 µm to about 1 µm. The base coat and the top coat can be applied with a thickness in the range of about 1 µm to about 7 µm. In an exemplary embodiment, the top coat can have a thickness that is at least about 50% less than a thickness of the base coat. A person skilled in the art will appreciate that the thicknesses of the coatings can vary depending on a particular application.

In another embodiment, a medical device such as a surgical needle can be coated with a single, homogeneous durable and lubricious coating composed generally of a combination of a vinyl-functionalized organopolysiloxane, for example, Momentive® Product Code No. MSC2631 silicone manufactured by Momentive® Performance Materials of Waterford, N.Y., and a hydroxyl terminated polydimethylsiloxane, for example, NuSil® Technologies Silicone Product No. MED4162 manufactured by NuSil® Technologies of Carpentaria, Calif., which may also include a crosslinker or catalyst. The single, homogeneous coating can be a homogeneous mixture of the vinyl-functionalized organopolysiloxane and the hydroxyl terminated polydimethylsiloxane such that when it is applied to a surface of a surgical needle, there is a single homogeneous layer formed thereon. For example, in some embodiments, the single, homogeneous coating can be a mixture of the top and base coatings noted above. In other embodiments, it can be any combination of the durable and lubricious materials noted herein. The single, homogeneous coating can be applied to the medical device in a single application step, and in some embodiments, the single, homogeneous coating can be formed of various ratios of the top and base coatings described above. The single, homogeneous coating can be applied directly to the surface of a medical device and can be the only coating applied to the medical device such that there is a single coating layer formed on the surface thereof.

In preparing an exemplary single, homogeneous coating composition, the vinyl-functionalized organopolysiloxane and the hydroxyl terminated polydimethylsiloxane can be prepared in various amounts, optionally with a catalyst and a crosslinker in a high viscosity solvent. In general, the vinyl-functionalized organopolysiloxane can be added to the composition in a range of about 2 wt. % to about 25 wt. %, and more preferably in a range of about 9 wt. % to about 19 wt. %. Likewise the hydroxyl terminated polydimethylsiloxane can be added to the composition in a range of about 2 wt. % to about 25 wt. %, and more preferably in a range of about 9 wt. % to about 19 wt. %. A high vapor pressure, low boiling point solvent, such as the HFE solvent can be added to the composition in a range of about 65 wt. % to about 85 wt. %, and more preferably in a range of about 70 wt. % to about 80 wt. %. In some embodiments, a catalyst and a crosslinker can be added to the composition. For example, a catalyst such as Momentive® Product Code No. SS8010 platinum catalyst, can be added in a range of about 0.002 wt. % to about 0.070 wt. %, and more preferably in a range of about 0.008 wt. % to about 0.05 wt. %. A crosslinker such as Momentive® Product Code No. SS4300 crosslinker, can be added in a range of about 0.01 wt. % to about 0.40 wt. %, and more preferably in a range of about 0.04 wt. % to about 0.28 wt. %.

Alternatively, the single, homogeneous coating composition can be prepared by combining the base coating and the top coating (both described above) in various ratios. Separate batches of each coating can be made and various amounts of the coating can be combined. For example, the ratio of the base coating to the top coating can be in the range of about 1:5 to 5:1, and more preferably in the range of about 1:3 to 3:1, for example, about 1:2, 1:1, 2:1, 1:3, 3:1, etc. As will be appreciated by those having ordinary skill in the art, any ratio combination of the top and base coatings can be used, including fractional ratios such as about a 0.5:1, a 1:0.5, a 1:1.5, a 1.5:1, a 1:2.5, a 2.5:1, etc.

In some embodiments, the single, homogeneous coating can be formed from a mixture of about 18.38 wt. % of the base silicone polymer, for example, the vinyl-functionalized organopolysiloxane, combined with about 72.85 wt. % of the HFE solvent. The base silicone polymer and the HFE solvent can be combined with about 8.667 wt. % of the silicone polymer, for example, the hydroxyl terminated polydimethylsiloxane. The Momentive® SS8010 platinum catalyst can then be added to the mixture in a suitable amount (e.g., about 0.0165 wt. %) and the Momentive® SS4300 crosslinker can be added at a suitable amount (e.g., about 0.0936 wt. %). The mixture can be agitated for a few minutes to ensure homogeneity, for example, for about one to two more minutes. This mixture is equivalent to, for example, about a 2:1 ratio (by weight) of the base and top coatings.

In another embodiment, an exemplary single, homogeneous coating can be formed from a mixture of about 13.78 wt. % of the base silicone polymer, for example, a vinyl-functionalized organopolysiloxane, combined with about 73.13 wt. % of the HFE solvent. The base silicone polymer and the HFE solvent can be combined with about 13.00 wt. % of the silicone polymer, for example, hydroxyl terminated polydimethylsiloxane. The catalyst can then be added to the mixture at about 0.0124 wt. % and the crosslinker can be added at about 0.0702 wt. %. This mixture is equivalent to, for example, about a 1:1 ratio (by weight) of the base and top coating solutions.

In still a further embodiment, the single, homogeneous coating can be formed from a mixture of about 9.189 wt. % of the base silicone polymer, for example, a vinyl-functionalized organopolysiloxane, combined with about 73.42 wt. % of the HFE solvent. The base silicone polymer and the HFE solvent can be combined with about 17.33 wt. % of the silicone polymer, for example, hydroxyl terminated polydimethylsiloxane. The catalyst can then be added to the mixture at about 0.083 wt. % and the crosslinker can be added at about 0.0468 wt. %. This mixture is equivalent to, for example, about a 1:2 ratio (by weight) of the base and top coating solutions.

As will be appreciated by those skilled in the art, there are various conventional methods of mixing the base and top coating solutions utilizing conventional processing equipment and techniques to achieve the different weight ratios within the single, homogeneous coating. In one method of mixing, master batches of the base coating and the top coating can each be mixed. The appropriate ratios of each coating can then be mixed together from the master batches to form the single, homogeneous coating. For example, if single, homogeneous coating with about a 2:1 ratio mixture of the base coating and the top coating are desired, then an amount of top coating can be mixed with double the amount of base coating, for example, about 20 grams of the base coating mixed with about 10 grams of the top coating. Or, if a single, homogeneous coating with about a 1:1 ratio is desired, then equal parts of the base and top coating can be mixed. In another embodiment, the combined single, homogeneous coating can be made directly with all components being added directly in their correct proportion, rather than mixing from separate master batches of the top and base coatings.

In some embodiments, a primer coating can optionally be applied to a medical device before the single, homogeneous coating. As noted above, the primer coat can have any formulation capable of bonding to a medical device and capable of providing an appropriate substrate for applying the single, homogeneous coating. In one embodiment, the primer coat can be formed of, for example, polyalkylsiloxane and tetraethyl silicate. A polyalkylsiloxane and tetraethyl silicate primer coat can be formulated for coating difficult-to-bond substrates such as, for example, tungsten-rhenium alloys. In other embodiments, a primer coating is not desired or required, and the single, homogeneous coating is applied directly to the substrate, i.e., the surface, of the medical device and is the only coating applied to the medical device. In still further embodiments, a surface of the medical device can include a primer coating as a part thereof and/or preformed thereon such that when the single, homogeneous coating is applied, there is only a single coating layer on the medical device.

The single, homogeneous coating can generally be applied at any thickness as needed. The thickness of the single, homogeneous coating should be sufficient to effectively provide the desired characteristics. For example, the single, homogeneous coating can be applied with a thickness in the range of about 1 μm to about 12 μm and more preferably from about 3 μm to about 6 μm or from about 1 μm to about 3.5 μm. If a primer coat is applied, it can be applied to have a thickness in the range of about 0.01 μm to about 1 μm. A person skilled in the art will appreciate that the thickness of the single, homogeneous coating and/or the primer coat can vary depending on a particular application.

There are many methods and systems contemplated herein that can be used to provide coated surgical needles or other medical devices. In general, a medical device such as a surgical needle can be produced from a desired material and prepared for coating, as described in more detail below. One or more coatings can be applied to the surgical needle to provide durability and lubricity during use. Before, during, and/or after application of any one of the coatings, the surgical needle can be cured for a sufficient amount of time effective to remove solvents in the coatings and/or to set, crosslink, and/or bond a coating.

Any process known in the art can be used to coat various medical devices with one or more of a base coat, a top coat, a single coat composed of a mixture of a base coat and a top coat (or the components of the base and top coat), and/or a primer coat including, but not limited to, dipping, spraying, wiping, brushing, total immersion, gravity feed, etc. For example, surgical needles can be dip coated in a number of traditional ways. If needles are being processed manually, the needles can be hand dipped or totally submersed in a coating. In a more automated process, coating solutions can be applied using a weir type circulating system in which surgical needles pass through the solution in an automatic fashion, either by robot or handling system. Dip techniques generally rely on surface tension for adhesion of the coating and wetting characteristics of the coating with relation to the substrate for continuity. A person skilled in the art will appreciate the various possible conventional processes, process equipment, and equivalents thereof, that can be used for the various techniques.

In one embodiment, one or more coatings can be applied to a surgical needle by spraying using, for example, ultrasonic and/or gas conformal coating spray nozzle systems and/or swirl coating systems. Ultrasonic and gas spray nozzles transmit energy to a liquid in an amount sufficient to atomize the liquid and form a spray of droplets. The spray of droplets can be applied to a medical device using a swirl process in which the droplets are swirled around the medical device in order to coat the substrate. Application of a coating using the swirl process can ensure a more even distribution of the coating to a surgical device while preventing excess collection of the coating that may result in drips, undesired pooling, droplets, and/or unevenness. Spraying also allows for precise control and adjustment of coating thickness. A particular coating can be applied to leave only a thin film on a surface or it can be applied to provide different thicknesses.

Different types and sizes of spray nozzles can be used depending on the specific coating compositions and the desired attributes of the spray stream generated. Spray nozzles can be designed to operate at specific frequencies and/or air pressures as needed and the desired power level for operating the nozzles can depend on various factors including the size and design of the nozzle, the viscosity of the composition being used, the volatility of components in the composition being used, etc. Both ultrasonic and fluid spray nozzles are available commercially.

Figure 3A:
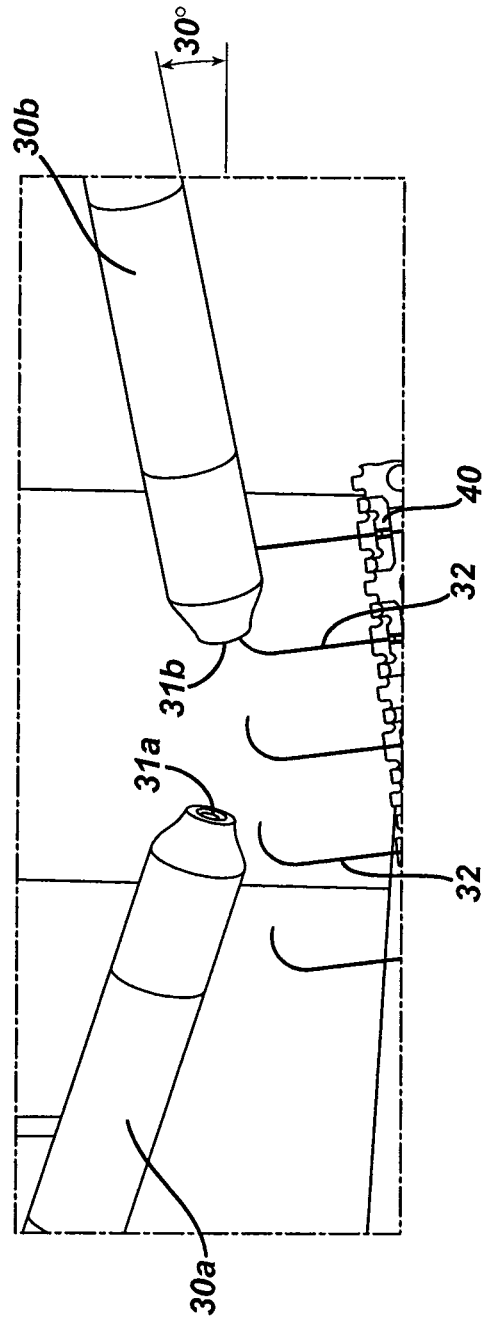
FIG. 3A is a perspective view of one exemplary embodiment of a swirl coating machine for swirl coating surgical needles.
Figure 3B:
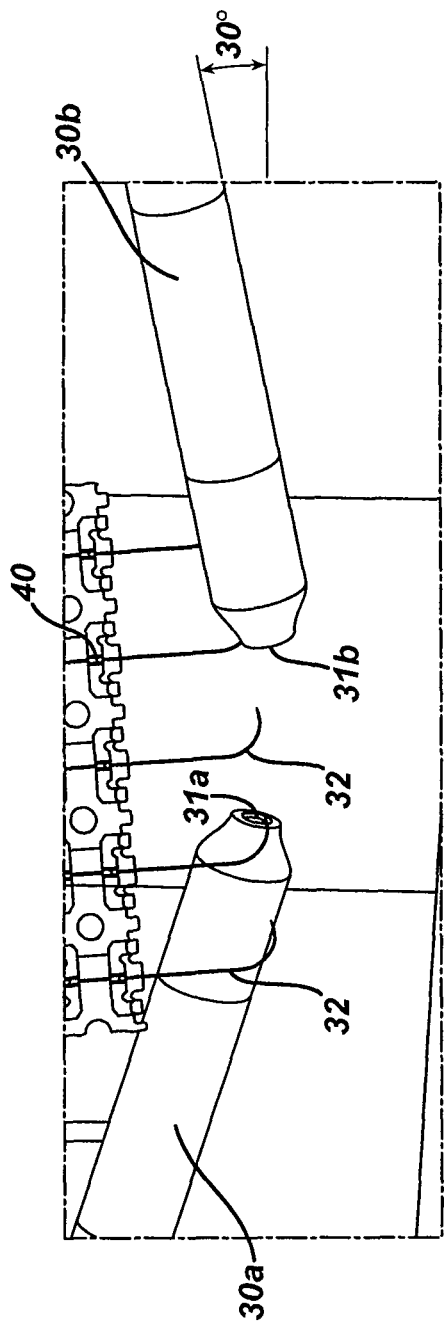
FIG. 3B is a perspective view of another exemplary embodiment of a swirl coating machine for coating suspended surgical needles.

In one embodiment, such as those illustrated in FIGS. 3A and 3B, opposed spray nozzles 30a, 30b are provided for applying a swirl coating to exemplary surgical needles 32. The opposed spray nozzles 30a, 30b can each be coupled to canisters holding a particular coating to be applied and can deliver the coating through discharge openings 31a, 31b. Each coating to be applied by the swirl process can be applied using different pairs of opposed spray nozzles 30a, 30b. Thus, in some embodiments, multiple sets of spray nozzles can be used to apply multiple coatings. Each spray nozzle 30a, 30b can have a fluted tip (not shown) for delivering the coating. An angle of the fluted tip, relative to a horizontal plane through which the needles extend perpendicular to, can be adjusted to focus the band of spray to optimize coating. As will be appreciated in the art, any angle can be used as needed to deliver a particular coating. In addition, different coatings may require delivery from a fluted tip with a different angle.

The opposed pair of spray nozzles 30a, 30b can extend from a positioner (not shown) capable of adjusting and maneuvering the spray nozzles 30a, 30b in three dimensions. The opposed spray nozzles 30a, 30b can be positioned in any way relative to each other as needed for a particular application and can generally be symmetrically opposed to one another. In the illustrated embodiment, the spray nozzles 30a, 30b are positioned at approximately about a 30 degree angle, as shown in FIGS. 3A-3B, relative to a horizontal surface. Horizontally, the nozzles 30a, 30b can be directly opposed, e.g., offset by about 180 degrees. Preferably, however, the nozzles 30a, 30b can be horizontally offset relative to each other by an amount less than about 180 degrees to prevent neutralization and to prevent overspray from collecting on the needles. The positioning of the opposed nozzles 30a, 30b can be optimized to provide the most complete coating of a surgical needle.

In general, the swirl coating can be applied during relative movement between the needles 32 and the nozzles 30a, 30b. In some embodiments, one or more needles 32 can remain stationary while the nozzles 30a, 30b move relative to the needles 32 while spraying the coating. In other embodiments, a carrier strip, such as the carrier strip 20 shown in FIG. 2, or a carrier strip 40 shown in FIGS. 3A and 3B, can move a plurality of surgical needles 32 relative to the opposed spray nozzles 30a, 30b while the nozzles 30a, 30b remain stationary. In other embodiments, both the carrier strip 40 and the nozzles 30a, 30b can move relative to one another. The carrier strip 40 can be mounted below the nozzles 30a, 30b as shown in FIG. 3A, or the carrier strip 40 can be mounted above the nozzles 30a, 30b as shown in FIG. 3B.

The movement speed of the carrier strip 40 and/or the nozzles 30a, 30b can be controlled so that the spray nozzles 30a, 30b provide optimal coverage and coating of the needles 32. For example, relative movement speed between the needles 32 and the nozzles 30a, 30b can be in the range of about 1 to about 15 inches per second. Optimally, the relative movement speed can be in the range of about 3 inches per second to about 5 inches per second. Shields may be optionally disposed between the nozzle discharge openings 31a, 31b and the proximal portion of the needle.

In some embodiments, a single, homogeneous coating can be applied to a medical device, such as a surgical needle, using the spray nozzles 30a, 30b. As noted above, when a single, homogeneous coating is utilized, it can be a mixture of the top and base coating described herein and/or a mixture of components designed to provide both lubricousness and durability. There are a number of ways that the single, homogeneous coating can be applied using the spray nozzles 30a, 30b. For example, the single, homogeneous coating can be premixed to the correct weight ratio of top and base coatings, for example, about 2:1 ratio, 1:1 ratio, and/or 1:2 ratio, and the premixed composition can be delivered by the nozzles 30a, 30b in a single, homogeneous coating layer on the medical device.

In another embodiment, the top coating can be delivered by one nozzle 30a, and the base coating can be delivered by the other nozzle 30b. In the case where about a 2:1 ratio of the top and base coatings is required, or about a 1:2 ratio of the top and base coatings is required, one nozzle 30a, 30b can be configured to deliver an amount of one coating while the other nozzle 30b, 30a is configured to deliver a different the amount (e.g., double or half of the amount) of the other coating such that the weight ratios are as desired.

In still a further embodiment, the top and base coatings can be provided into canisters in fluid communication with the nozzles 30a, 30b and the two coatings can be mixed into the desired ratio within the nozzles 30a, 30b prior to being applied to the medical device. For example, the nozzles 30a, 30b can have a mixing mechanism, such as two feed lines, associated therewith that can mix about a 2:1 ratio, a 1:1 ratio, a 1:2 ratio, and/or any other ratio desired, of the top and base coatings such that the single, homogeneous coating is premixed within the nozzles 30a, 30b before it is applied to the medical device.

There are many mechanisms known in the art for curing, hardening, and/or setting a coating on a surgical device such a surgical needle. Curing can also cause evaporation of any solvent used in making the coating. Curing can generally be accomplished through exposure of a coated surgical needle to some form of temperature increase and/or humidity change for a predetermined period of time. For example, the coated needles can be placed in a furnace or oven, a hotbox, a humidification chamber, and/or an infrared chamber, among other forms known in the art. Curing times can range from "flash" curing of only a few seconds to times longer than twenty-four hours.

During the curing process, the temperature and/or humidity can be maintained at a single value for the entire time and/or it can be increased or decreased as needed over time. Temperature can be monitored and adjusted using, for example, a thermocouple and a potentiometer to control power to heating elements. The potentiometer can be preconfigured so that temperature measurements made by the thermocouple at periodic increments along a length of the heating system are maintained at or between a specified temperature range. In other embodiments, temperature can be controlled using a feedback loop where temperature measurements that correlate to temperatures where surgical needles will pass are fed back to a power supply that continuously adjusts power delivered to the heated filaments to maintain a desired temperature range. A humidity monitor can be used to monitor and adjust humidity. In some embodiments, each coating can be cured after application thereof to the surgical needle. In other embodiments, all coatings can be applied before initiating the curing process.

In one embodiment, an infrared emitter can be used to effect curing of a coating Infrared emitters are available commercially from Heraeus® Noblelight, for example, Model SKL200-800. The actual emitters can include, for example, eight foot long thin heated filaments embedded within a reflective channel used to focus and contain the heat. The infrared heating system can be oriented so that the channel's opening is facing down. Surgical needles to be cured in the infrared heating system can be held vertically and passed between two concave reflective walls of the channel at about, for example, ¼ inch from the heated filaments. Needles can be held on a carrier strip as they traverse the channel at a speed in the range of about 3 inches per second to about 5 inches per second, although any speed can be used.

Figure 4A:
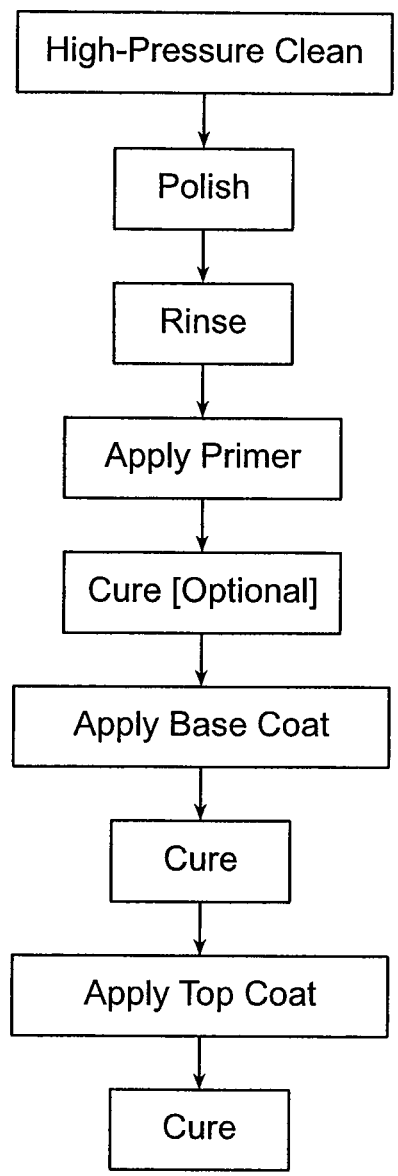
FIG. 4A is a flowchart of one exemplary method for manufacturing and coating surgical needles using two coatings.
Figure 4B:
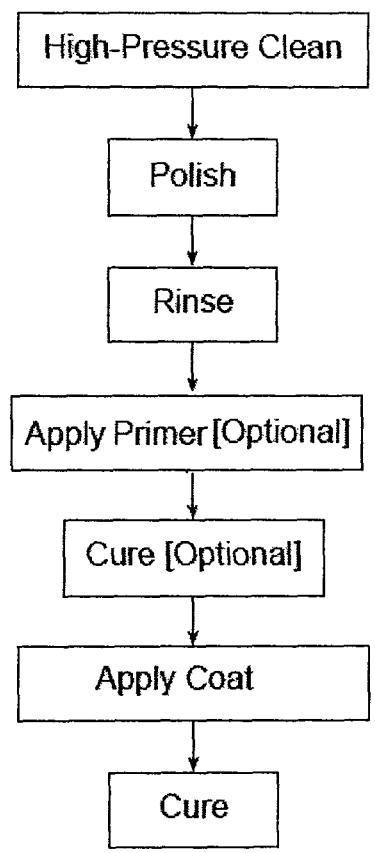
FIG. 4B is a flowchart of one exemplary method for manufacturing and coating surgical needles using a single, homogeneous coating.

While many methods for providing durable lubricious coatings on surgical needles are contemplated, a flow chart of an embodiment of one particular method is illustrated in FIG. 4A. As shown, the method can generally include manufacturing the surgical needles, preparing the surface of the needles for receiving a coating, coating the needles with a primer coat, base coat, and/or top coat, and curing the coatings. In another embodiment illustrated in FIG. 4B, the method can generally include manufacturing the surgical needles, preparing the surface of the needles for receiving a coating, optionally coating the needles with a primer coat, coating the needle with a single, homogeneous coating, and curing the single, homogeneous coating. A person skilled in the art will appreciate the variations and additions that can be included in such methods.

In manufacturing the surgical needles, raw wire of a suitable composition can be unspooled and cut into blanks for shaping. While any size blanks can be used depending on the size of the needle desired, in one embodiment, the wire can be cut into two inch blanks. Once cut, the blanks can be attached to a metal carrier strip, such as that illustrated in FIG. 2. The blanks can be secured and shaped into their preferred needle form by any methods known in the art, including forming, grinding, curving, etc.

Needles that are appropriately shaped can be cleaned to remove contaminates and to prepare the surface for receiving a coating. For example, the needles can be exposed to high pressure nozzles that release water at high temperature and pressure. In other embodiments, the needles can be baked to high temperatures to release any contaminates. Once the needles have been cleaned, they can be electropolished for any amount of time necessary. The needles can be immersed in the electropolish bath (e.g., sodium hydroxide, phosphoric acid, etc.) and subjected to direct current to remove ions at a controlled rate. Once complete, the needles can be rinsed successive times, for example, two times, in de-ionized water baths.

In some embodiments, a primer coat, such as the SS4044P primer described above, can be applied to the newly manufactured and cleaned surgical needles. The primer coating can be used, for example, when the needle is a tungsten-rhenium alloy. The primer can be applied using any method known in the art including dipping or spraying, but in one embodiment, the primer is applied to the surgical needles by dipping. Using a grasper or carrier strip, the needles can be dipped into the primer at room temperature for one to two seconds to effect complete coverage thereof. A person skilled in the art will appreciate that primers can be applied at any temperature and for any length of time as appropriate for a particular primer. Reactive functional groups in the primer can react with the functional hydroxide groups in the surface of the surgical needles and covalently bond thereto. In some embodiments, after the primer coating has been applied, the surgical needle can be flash cured for about 20 seconds at an appropriate temperature, for example, about 200 degrees Celsius. Once cured, the primer can create a boundary between the surface of the surgical needle and any later applied coatings.

In some embodiments, a base coat, such as the Momentive® base coat described above, can be applied to the external surface of the surgical needle, and over a primer if utilized, for example, the SS4044P primer. Any application method known in the art can be used, but in one embodiment, the surgical needle is sprayed or swirl coated with the base coat using opposed spray nozzles. For example, the surgical needle can be passed between first and second opposed spray nozzles to be coated. Application of the base coat using the spray or swirl coating ensures an evenly distributed layer of the base coat on the needle or over the primer, if utilized. As the base coat is applied, the solvent, for example, the HFE solvent, can rapidly evaporate to leave a thin layer of evenly distributed silicone on the needle surface. In some embodiments, the base coat can be cured onto the surface by exposure to an "in-line" infrared heating system. The base coat can be exposed to a number of different wavelengths of infrared light and cured.

The coated medical device of the invention may also have a top coat applied over the base coat, more preferably after the base coat is partially cured. For example, the NuSil® top coat described above can be applied over the Momentive® base coat. Any application method known in the art can be used, but in one embodiment, the surgical needle can be sprayed or swirl coated with the top coat using opposed spray nozzles. For example, the surgical needle can be passed between third and fourth opposed spray nozzles to be coated. Application of the top coat using the spraying or swirl coating technique ensures an evenly distributed layer of the top coat over the base coat. As the top coat is applied, the solvent, for example, the HFE solvent, can rapidly evaporate to leave a thin layer of evenly distributed top coat over the base coat. In some embodiments, after application of the top coat, the top coat can be flashed cured to drive off any excess solvent. The needles can be passed through, for example, a hot box or other heated curing system, for any time and at any temperature necessary to accomplish evaporation of the solvent. In one embodiment, the top coat can be flashed cured in an infrared heater for approximately 20 seconds at a temperature in the range of about 165 degrees Celsius to about 200 degrees Celsius.

In other embodiments, a single, homogeneous coating can be applied to the external surface of the surgical needle, and over a primer if utilized, for example, the SS4044P primer. The single, homogeneous coating can be, for example, a combination of the Momentive® base coat and the NuSil® top coat described above, although any suitable combination of materials can be used to form the single, homogeneous coating. Any application method known in the art can be used, but in one embodiment, the surgical needle is sprayed or swirl coated with the single, homogeneous coating using opposed spray nozzles. For example, the surgical needle to be coated can be passed between first and second opposed spray nozzles. Application of the single, homogeneous coating using the spray or swirl coating ensures an evenly distributed layer of the single, homogeneous coating on the needle or over the primer coat of the needle, if utilized. As the single, homogeneous coating is applied, the solvent, for example, the HFE solvent, can rapidly evaporate to leave a thin layer of the single, homogeneous coating on the needle surface. In some embodiments, the single, homogeneous coating can be cured by exposure to an "in-line" infrared heating system for a sufficiently effective period of time such as, for example, from about 1 second to about 60 seconds, from about 10 seconds to about 30 seconds, and/or for about 20 seconds. The single, homogeneous coating can be exposed to a number of different wavelengths of infrared light and cured. The single, homogeneous coating can also be cured in an oven at a temperature in the range of about 60 degrees Celsius to about 180 degrees Celsius for a time in the range of about 1 hour to about 5 hours, from about 2.5 hours to about 3.5 hours, and/or more preferably for about 3 hours at a temperature in the range of about 100 degrees Celsius to about 140 degrees Celsius.

Following application of the top coat and/or of the single, homogeneous coating, the surgical needles can be optionally re-spooled. In some embodiments, the coated surgical needles can be exposed to a final curing process. For example, the re-spooled needles can be placed inside a convection oven and cured at a temperature and time sufficient to further cure the coating. In one embodiment, the surgical needles can be cured in the convection oven for approximately four hours at about 165 degrees Celsius. In other embodiments, the final cure can be performed at a temperature of about 80 degrees Celsius for approximately three hours.

The cure times for the exemplary coatings and methods described herein are extremely beneficial in that they are significantly less than cure times for previous coatings and methods known in the art. Previous coatings and methods could require curing of the surgical needles for up to 72 hours plus processing and coating time. The currently described exemplary coatings and methods can reduced the total curing time to less than about 4 hours and possibly less than about 15 minutes, providing a significant increase in efficiency for manufacturing of the needles. With the use of the single, homogeneous coating, the cure time can be reduced even further to less than about 1 minute.

The use of two coatings as described above, and/or of a single, for example, continuous coating as also described above, results in surgical needles that exhibit reduced and/or generally constant tissue penetration force compared with standard surgical needles after an equivalent number of passes through tissue. Thus, both the lubricity of the needle as well as the durability of the coating is improved. This effect is believed to result for a number of reasons. For example, application of the base and top coats using a swirl coating process provides an even distribution of the coatings over the substrate. This is most clearly represented in FIG. 6, which will be described in more detail below. In addition, the compositions of the coatings in combination with the methods of application and curing can result in significantly decreased average force required to repeatedly pass the needle through synthetic media, as shown in FIG. 7, which will also be described in more detail below.

The use of the optional primer coating can also be advantageous. A primer coating can be capable of chemically bonding to the needle surface to provide a bonding substrate for the lubricious silicone coatings to adhere to, resulting in increased durability of the base and top coatings. For example, FIG. 5 illustrates the force required to pass a needle through synthetic media in relation to the number of passes through synthetic media. As shown, needles without primer have a drastic rise in the force required after thirty passes when compared with primed needles of identical material and configuration, which tend to maintain a fairly constant force up to at least thirty passes through synthetic media. More detail will be presented in the examples described below.

Coating performance for medical devices can generally be tested with a variety of conventional tests. In the case of surgical needles, coating performance and integrity is evaluated using a penetration test device. A portion of a coated surgical needle is held using a holding device, and the coated needle is then partially passed through a synthetic or natural penetratable material some number of times. The material is typically a type of polymer or synthetic leather, for example, Permair, Rubber-Cal, Monmouth rubber, Porvair, etc. The needle can be passed through the penetratable material for about one to about twenty times, between about one to about twenty-five times, and most preferably between about one to about thirty times. The needle is then retracted from the media. The maximum force is recorded for each pass and is used as a measure of the coating performance. Various attributes of coating performance can be tested using these techniques.

EXAMPLES

The following experiments were conducted to examine the effects of varying the needle coating materials and methods. For each test, the needles were passed through Monmouth Duraflex MR40 NBR rubber membrane ("Monmouth rubber"), which serves to simulate flesh, or human cadaver tissue. In the following non-limiting examples, from 4 to 10 needles were used and individually passed through the penetration membrane thirty times each. The maximum force in grams was recorded for each pass and used as a measure of coating performance.

The surgical needles were mounted in a rotating stage to fix the needle in a position perpendicular to the penetration membrane surface and oriented on its radial profile with the axis of rotation on the same plane as the plane of the penetration membrane. The needle was rotated into the penetration membrane, which was mounted on top of the load cell. The maximum amount of vertical force was recorded as the needle was pushed through the penetration membrane.

The following non-limiting examples serve to further illustrate the principles and practice of the present invention:

Example 1

The following tests were performed to examine the effect coating methods have on the force required to pass a needle through Monmouth rubber synthetic media. The performance of needles that were dip coated was compared with the performance of needles that were spray/swirl coated.

Test A

In Test A, five needles were prepared for penetration testing. The needles were made from ETHALLOY® Alloy stainless steel and had a diameter of 0.0105 inches. A base coating composition was prepared from a mixture of 20 wt. % of Micropro 600 and Micromatte 2000, produced by Micropowders Inc., mixed with 80 wt. % of HFE-72DE solvent. The MicroPro and Micromatte powder weight ratio was at 4:1. Five test needles were each dipped into the base coating to coat their surfaces. The needles were coated by hand via the dipping process and placed on a magnetic tray. The tray includes raised magnetic strips for holding the proximal ends of the needles secure during the curing cycle and transport while the distal end (tip) of the needles hang over the edge of the magnetic strips. This configuration prevents the needle tips from making contact with the tray. The coated needles were then heated to 190 degrees Celsius in a convection oven for ninety minutes at ambient atmosphere. The needles were then allowed to cool at ambient temperature outside of the oven.

A top coating composition was prepared using 26 wt. % of NuSil® MED4162 with 74 wt. % HFE-72DE solvent. The five needles were then each hand dipped into the top coating composition. The needles were then heated to 220 degrees Celsius in a convection oven and cured for four hours at ambient atmosphere. The needles were allowed to cool at ambient temperature outside of the oven.

Once cured, the five needles were each passed through the penetration membrane thirty times and the penetration force in grams was recorded as shown in Table 1 below.

ing System available from Asymtek® of Carlsbad, Calif. with the following parameters: 2 PSI fluid pressure, 50 PSI air assist, and 10 in/sec line speed. The coated needles were then heated to 190 degrees Celsius in a convection oven and cured for ninety minutes at ambient atmosphere. The needles were allowed to cool at ambient temperature outside of the oven.

TABLE 1

| Experiment | Needle | Pass Penetration [g] | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| A | 1 | 39 | 38 | 41 | 40 | 42 | 47 | 42 | 46 | 43 | 47 | 47 | 46 | 48 | 49 | 52 |
| | 2 | 40 | 42 | 45 | 46 | 46 | 49 | 50 | 55 | 51 | 51 | 56 | 53 | 56 | 57 | 63 |
| | 3 | 40 | 41 | 41 | 47 | 45 | 46 | 49 | 51 | 51 | 45 | 50 | 52 | 52 | 57 | 54 |
| | 4 | 34 | 34 | 36 | 36 | 36 | 36 | 38 | 37 | 40 | 39 | 42 | 41 | 44 | 43 | 45 |
| | 5 | 38 | 38 | 38 | 40 | 42 | 44 | 47 | 45 | 48 | 48 | 46 | 50 | 49 | 52 | 51 |
| | St Dev | 2.5 | 3.1 | 3.4 | 4.6 | 3.9 | 5.0 | 5.1 | 6.8 | 4.9 | 4.5 | 5.2 | 4.9 | 4.5 | 5.9 | 6.5 |
| | Avg | 38.2 | 38.6 | 40.2 | 41.8 | 42.2 | 44.4 | 45.2 | 46.8 | 46.6 | 46.0 | 48.2 | 48.4 | 49.8 | 51.6 | 53.0 |

| Experiment | Needle | Pass Penetration [g] | | | | | | | | | | | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| A | 1 | 53 | 45 | 53 | 57 | 48 | 56 | 53 | 55 | 56 | 54 | 57 | 57 | 57 | 60 | 61 |
| | 2 | 59 | 54 | 64 | 62 | 65 | 69 | 62 | 66 | 68 | 68 | 71 | 75 | 73 | 72 | 69 |
| | 3 | 56 | 55 | 58 | 56 | 57 | 60 | 61 | 59 | 62 | 61 | 61 | 62 | 60 | 64 | 62 |
| | 4 | 45 | 45 | 46 | 48 | 49 | 48 | 49 | 51 | 53 | 53 | 50 | 53 | 52 | 56 | 53 |
| | 5 | 51 | 51 | 52 | 50 | 54 | 51 | 56 | 52 | 57 | 59 | 53 | 58 | 61 | 58 | 58 |
| | St Dev | 5.3 | 4.8 | 6.8 | 5.6 | 6.9 | 8.2 | 5.4 | 6.1 | 5.9 | 6.0 | 8.2 | 8.5 | 7.8 | 6.3 | 5.9 |
| | Avg | 52.8 | 50.0 | 54.6 | 54.6 | 54.6 | 56.8 | 56.2 | 56.6 | 59.2 | 59.0 | 58.4 | 61.0 | 60.6 | 62.0 | 60.6 |

Test B

In Test B, five needles were prepared for penetration testing. The needles were made from ETHALLOY® Alloy stainless steel and had a diameter of 0.0105 inches. A base coating composition was prepared from a mixture of 20 wt. % of Micropro 600 and Micromatte 2000, produced by Micropowders Inc., mixed with 80 wt. % of HFE-72DE solvent. The MicroPro and Micromatte powder weight ratio was at 4:1. The five test needles were swirl coated with the base coating composition using a single pass spray using the SC-300 Swirl Coat™ Applicator and the Century® C-341 Conformal Coat- A top coating composition was prepared using 26 wt. % of NuSil® MED4162 with 74 wt. % HFE-72DE solvent. The five test needles were swirl coated with the top coating composition using a single pass spray with the following parameters: 10 PSI fluid pressure, 50 PSI air assist, and 5 in/sec line speed. The needles were then cured for four hours at 220 degrees Celsius. Once cured, the five needles were each passed through the penetration membrane thirty times and the penetration force in grams was recorded as shown in Table 2 below.

TABLE 2

| Experiment | Needle | Pass Penetration [g] | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| B | 1 | 30 | 29 | 30 | 31 | 31 | 31 | 33 | 33 | 31 | 32 | 34 | 34 | 34 | 35 | 36 |
| | 2 | 33 | 32 | 31 | 35 | 33 | 34 | 34 | 35 | 34 | 35 | 35 | 36 | 36 | 35 | 37 |
| | 3 | 29 | 28 | 29 | 30 | 30 | 30 | 31 | 31 | 32 | 32 | 32 | 33 | 34 | 32 | 32 |
| | 4 | 29 | 29 | 29 | 28 | 29 | 30 | 31 | 30 | 32 | 33 | 33 | 33 | 35 | 35 | 34 |
| | 5 | 32 | 31 | 33 | 33 | 32 | 32 | 35 | 34 | 34 | 33 | 34 | 35 | 36 | 35 | 36 |
| | St Dev | 1.8 | 1.6 | 1.5 | 2.9 | 1.6 | 1.7 | 1.8 | 2.1 | 1.3 | 1.2 | 1.1 | 1.3 | 1.0 | 1.3 | 2.0 |
| | Avg | 30.6 | 29.8 | 30.6 | 31.2 | 31.0 | 31.4 | 32.8 | 32.6 | 32.6 | 33.0 | 33.6 | 34.2 | 35.0 | 34.4 | 35.0 |

| Experiment | Needle | Pass Penetration [g] | | | | | | | | | | | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| B | 1 | 34 | 38 | 37 | 36 | 37 | 38 | 37 | 38 | 37 | 40 | 40 | 39 | 37 | 39 | 42 |
| | 2 | 37 | 37 | 39 | 38 | 38 | 37 | 38 | 39 | 38 | 39 | 40 | 39 | 40 | 40 | 41 |
| | 3 | 35 | 33 | 33 | 34 | 35 | 34 | 35 | 35 | 36 | 35 | 34 | 34 | 36 | 36 | 37 |
| | 4 | 36 | 36 | 37 | 37 | 38 | 38 | 38 | 39 | 39 | 38 | 40 | 41 | 41 | 38 | 41 |
| | 5 | 38 | 36 | 37 | 34 | 37 | 37 | 36 | 37 | 37 | 37 | 39 | 39 | 38 | 39 | 39 |
| | St Dev | 1.6 | 1.9 | 2.2 | 1.8 | 1.2 | 1.6 | 1.3 | 1.7 | 1.1 | 1.9 | 2.6 | 2.6 | 2.1 | 1.5 | 2.0 |
| | Avg | 36.0 | 36.0 | 36.6 | 35.8 | 37.0 | 36.8 | 36.8 | 37.6 | 37.4 | 37.8 | 38.6 | 38.4 | 38.4 | 38.4 | 40.0 |

Figure 6:
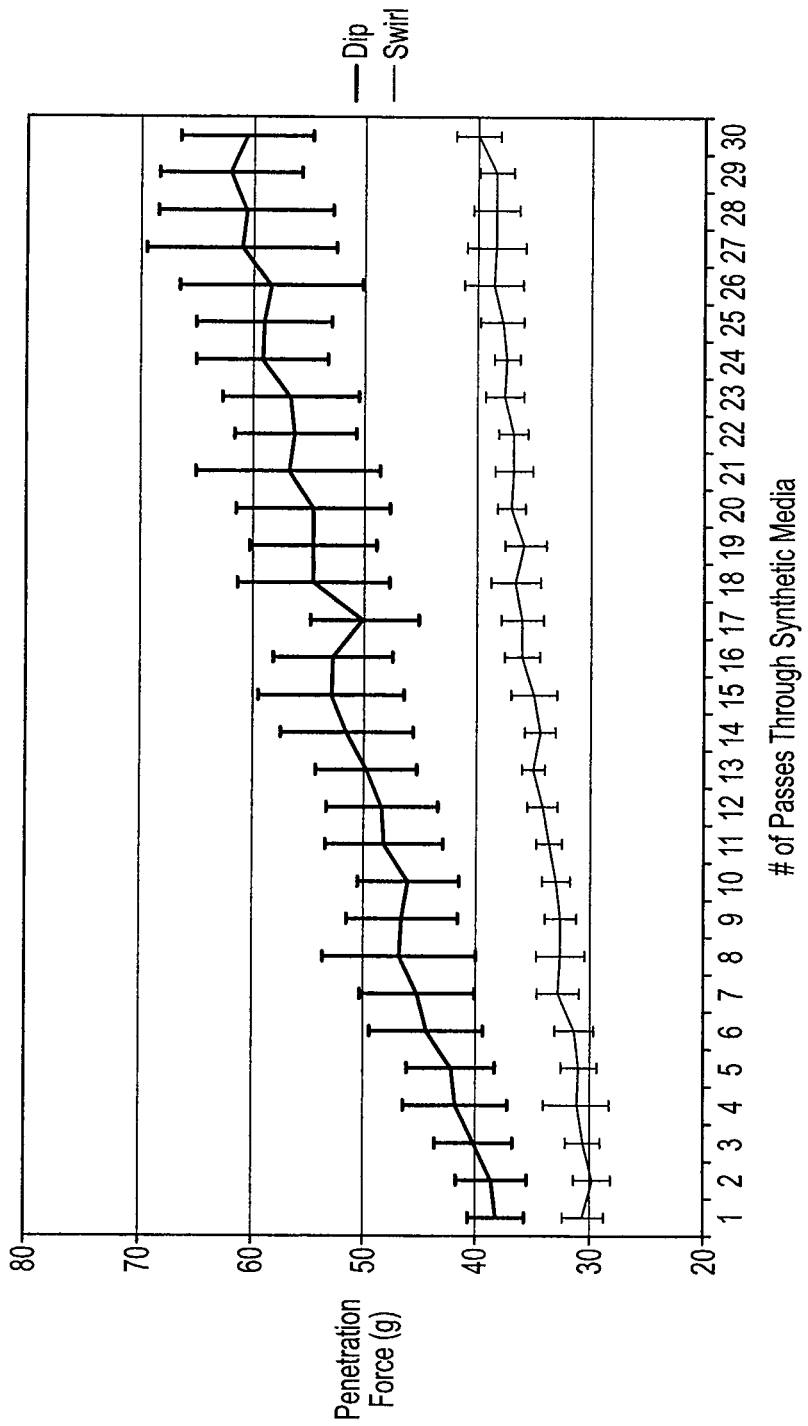
FIG. 6 is graphical representation comparing the force required to pass surgical needles that are swirl coated through synthetic media versus surgical needles that are dip coated.
Figure 7:
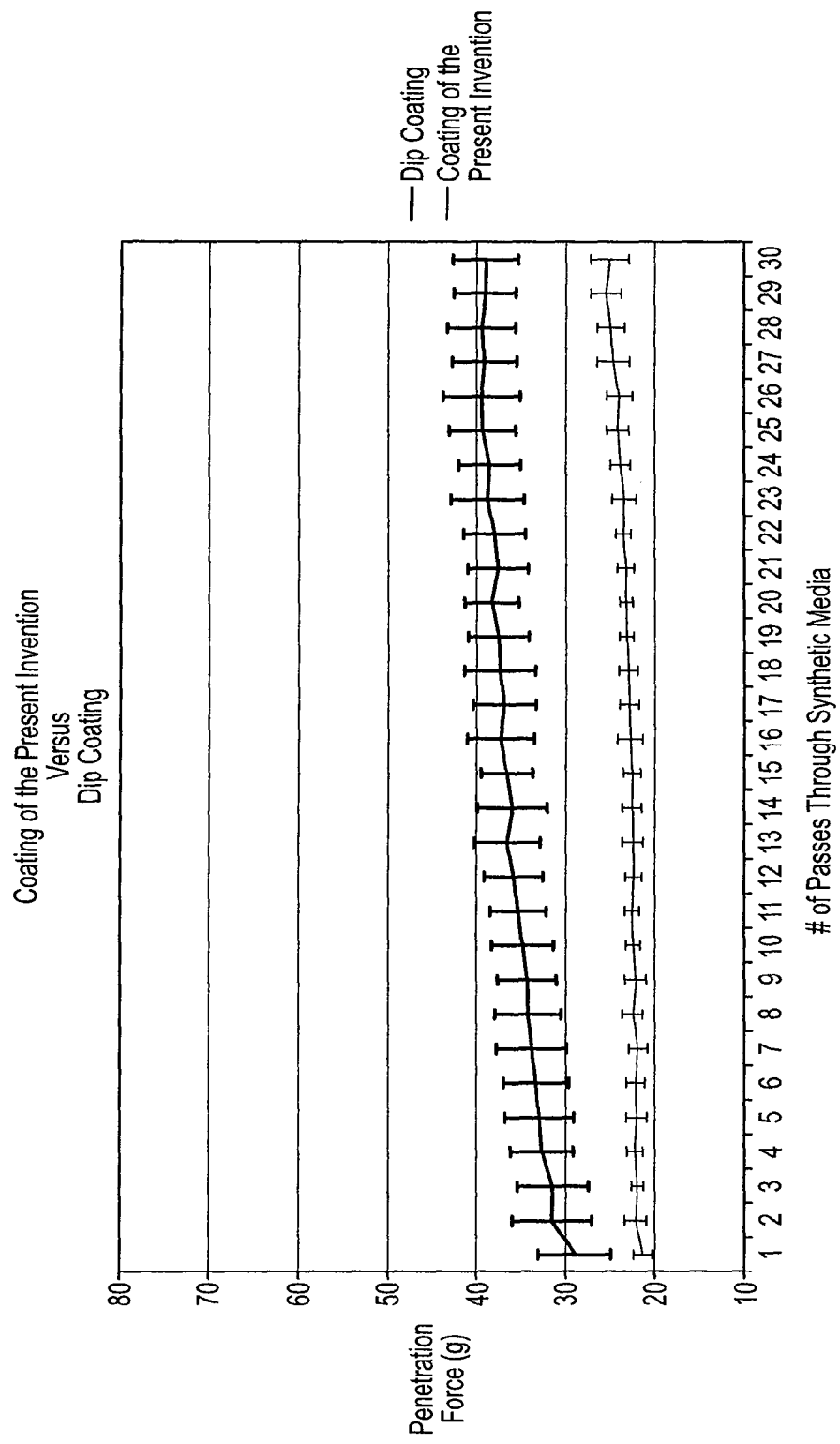
FIG. 7 is a graphical representation comparing forces associated with two different coating compositions and application methods.

FIG. 6 is a graphical representation of the averaged results of Tests A and B in direct comparison. The y-axis shows the penetration force in grams needed to pass a needle through the penetration membrane. The x-axis shows the number of passes. The thick solid line represents the needles that were dip coated with the base and top coating compositions, as set forth in Test A, while the thin solid line represents the needles that were swirl coated with the base and top coating compositions, as set forth in Test B.

As can be seen, the needles that were dip coated had an initial penetration force of about 38 g. The penetration force increased steadily over the thirty passes, and the needles required an average maximum force of 61 g after thirty passes. In contrast, the needles that were swirl coated had an initial penetration force of about 31 g. The penetration force remained substantially constant over the thirty passes, with the average maximum force after thirty passes being about 40 g. As shown, the needles that were swirl coated required about 7 g less force in the beginning on average than the needles that were dip coated, and the force remained substantially constant. Ultimately, the swirl coated needles required about 21 g less maximum force after thirty passes than the dip coated needles.

Example 2

The penetration performance of various coating compositions and coating methods were also tested. In the following Tests A and B, two different types of needle coating compositions and application methods were examined. The needles were passed through Monmouth rubber synthetic media.

Test A

In Test A, ten commercially available Ethicon BV-175 surgical needles having a 0.0078 inch diameter were tested. A coating was applied using a double dipping procedure. In particular, a silicone dip was prepared using a concentration of NuSil® Product No. MED4162 mixed with Micropro 600 and Micromatte 2000 powders for lubrication as described above. The needles were placed on a moving carrier strip and dipped a first time. The needles were then flash cured in a hot box at approximately 225 degrees Celsius for thirty seconds. The needles were then cured for 36 hours in a convection oven at 163 degrees Celsius. The needles were dipped a second time, flash cured, and then cured in a convection oven for another 36 hours.

As shown in Table 3 below, ten needles were tested with thirty passes through the penetration membrane.

TABLE 3

| | | Pass Penetration [g] | | | | | | | | | | | | | | |
|---|---|---|---|---|---|---|---|---|---|---|---|---|---|---|---|---|
| Experiment | Needle | 1 | 2 | 3 | 4 | 5 | 6 | 7 | 8 | 9 | 10 | 11 | 12 | 13 | 14 | 15 |
| A | 1 | 35 | 38 | 37 | 38 | 38 | 38 | 38 | 39 | 38 | 38 | 40 | 40 | 41 | 42 | 41 |
| | 2 | 35 | 37 | 37 | 37 | 38 | 39 | 40 | 40 | 39 | 40 | 38 | 40 | 41 | 40 | 39 |
| | 3 | 26 | 26 | 27 | 28 | 28 | 28 | 28 | 29 | 29 | 30 | 31 | 31 | 31 | 30 | 34 |
| | 4 | 28 | 29 | 31 | 32 | 32 | 32 | 32 | 33 | 33 | 33 | 34 | 34 | 34 | 33 | 34 |
| | 5 | 28 | 34 | 31 | 32 | 33 | 34 | 35 | 34 | 34 | 34 | 34 | 35 | 35 | 35 | 36 |
| | 6 | 27 | 28 | 28 | 31 | 30 | 30 | 31 | 32 | 32 | 32 | 34 | 34 | 35 | 32 | 34 |
| | 7 | 34 | 35 | 36 | 37 | 38 | 37 | 38 | 38 | 38 | 39 | 39 | 40 | 40 | 39 | 41 |
| | 8 | 27 | 34 | 32 | 33 | 34 | 34 | 35 | 35 | 36 | 37 | 38 | 37 | 40 | 39 | 38 |
| | 9 | 25 | 28 | 27 | 29 | 30 | 31 | 31 | 33 | 34 | 35 | 35 | 36 | 37 | 37 | 36 |
| | 10 | 25 | 27 | 29 | 30 | 29 | 31 | 31 | 30 | 31 | 31 | 31 | 32 | 32 | 33 | 34 |
| | St Dev | 4.1 | 4.5 | 4.0 | 3.5 | 3.9 | 3.7 | 3.9 | 3.7 | 3.3 | 3.5 | 3.2 | 3.3 | 3.7 | 4.0 | 2.9 |
| | Avg | 29.0 | 31.6 | 31.5 | 32.7 | 33.0 | 33.4 | 33.9 | 34.3 | 34.4 | 34.9 | 35.4 | 35.9 | 36.6 | 36.0 | 36.7 |

| | | Pass Penetration [g] | | | | | | | | | | | | | | |
|---|---|---|---|---|---|---|---|---|---|---|---|---|---|---|---|---|
| Experiment | Needle | 16 | 17 | 18 | 19 | 20 | 21 | 22 | 23 | 24 | 25 | 26 | 27 | 28 | 29 | 30 |
| A | 1 | 40 | 40 | 42 | 43 | 42 | 40 | 42 | 42 | 43 | 42 | 44 | 43 | 41 | 40 | 43 |
| | 2 | 44 | 39 | 43 | 39 | 41 | 40 | 40 | 44 | 40 | 43 | 42 | 40 | 40 | 42 | 40 |
| | 3 | 31 | 33 | 30 | 32 | 34 | 33 | 33 | 34 | 35 | 34 | 33 | 34 | 35 | 34 | 35 |
| | 4 | 36 | 35 | 36 | 37 | 38 | 37 | 36 | 35 | 36 | 38 | 38 | 38 | 38 | 38 | 38 |
| | 5 | 36 | 35 | 36 | 38 | 37 | 37 | 37 | 38 | 38 | 40 | 38 | 39 | 36 | 38 | 38 |
| | 6 | 35 | 33 | 35 | 35 | 36 | 34 | 35 | 35 | 35 | 36 | 36 | 36 | 36 | 36 | 36 |
| | 7 | 41 | 41 | 40 | 40 | 40 | 41 | 41 | 42 | 42 | 40 | 42 | 42 | 45 | 41 | 41 |
| | 8 | 39 | 41 | 40 | 39 | 40 | 40 | 41 | 42 | 40 | 40 | 42 | 43 | 43 | 40 | 40 |
| | 9 | 38 | 40 | 39 | 40 | 42 | 42 | 42 | 43 | 43 | 46 | 46 | 43 | 45 | 46 | 46 |
| | 10 | 34 | 33 | 34 | 33 | 34 | 33 | 34 | 34 | 34 | 35 | 34 | 34 | 36 | 36 | 34 |
| | St Dev | 3.8 | 3.5 | 4.0 | 3.4 | 3.1 | 3.4 | 3.5 | 4.1 | 3.5 | 3.7 | 4.4 | 3.6 | 3.9 | 3.5 | 3.7 |
| | Avg | 37.4 | 37.0 | 37.5 | 37.6 | 38.4 | 37.7 | 38.1 | 38.9 | 38.6 | 39.4 | 39.5 | 39.2 | 39.5 | 39.1 | 39.1 |

Test B

In Test B, ten Ethicon tungsten-rhenium alloy needles having an 0.008 inch diameter were tested. The needles were prepared by applying the Momentive® SS4044P primer coat at room temperature. The primer coat was flash cured at 200 degrees Celsius for 2-3 seconds. A base coating composition was then applied over the primer using swirl coating techniques. The base coating composition was made by combining 27.58 wt. % of Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, polymethyl hydrogen siloxane, product no. SS4300 was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator. The needles were again flash cured at a temperature of 190 degrees Celsius for approximately thirty seconds.

The needles included in Test B were then batch cured at 80 degrees Celsius for three hours in a convection oven. The needles were tested by passing each needle thirty times through the penetration membrane. The force required to do so is set forth in Table 4.

Example 3

The following tests were performed to examine the effect coating methods have on the force required to pass a needle through Monmouth rubber synthetic media. The performance of needles that were dip coated was compared with the performance of needles that were spray/swirl coated.

Test A

In Test A, four 0.026 inch diameter needles made from ETHALLOY® Alloy and having a taper cut point geometry were prepared for penetration testing. A base coating composition was prepared from a solution of 2.5 g of Momentive®, vinyl siloxane polymer, product no. MSC2631, 22.15 g of

TABLE 4

| Experiment | Needle | Pass Penetration [g] | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| B | 1 | 22 | 22 | 22 | 23 | 23 | 22 | 22 | 23 | 21 | 23 | 23 | 22 | 22 | 22 | 22 |
| | 2 | 22 | 24 | 23 | 23 | 22 | 21 | 22 | 22 | 22 | 23 | 24 | 23 | 23 | 22 | 23 |
| | 3 | 21 | 21 | 23 | 22 | 21 | 21 | 20 | 22 | 22 | 21 | 22 | 21 | 21 | 22 | 22 |
| | 4 | 21 | 21 | 22 | 22 | 24 | 23 | 24 | 24 | 25 | 23 | 23 | 24 | 24 | 24 | 24 |
| | 5 | 21 | 21 | 22 | 23 | 22 | 22 | 21 | 22 | 21 | 22 | 22 | 22 | 22 | 22 | 22 |
| | 6 | 20 | 22 | 22 | 22 | 22 | 24 | 22 | 22 | 22 | 23 | 23 | 22 | 22 | 22 | 23 |
| | 7 | 21 | 23 | 22 | 22 | 21 | 22 | 22 | 23 | 22 | 23 | 21 | 23 | 22 | 22 | 22 |
| | 8 | 21 | 23 | 22 | 23 | 23 | 23 | 22 | 24 | 23 | 23 | 23 | 23 | 24 | 23 | 23 |
| | 9 | 24 | 24 | 21 | 23 | 23 | 23 | 23 | 23 | 23 | 23 | 23 | 23 | 24 | 25 | 24 |
| | 10 | 21 | 21 | 21 | 20 | 20 | 21 | 21 | 20 | 21 | 21 | 22 | 21 | 21 | 22 | 21 |
| | St Dev | 1.1 | 1.2 | 0.7 | 0.9 | 1.2 | 1.0 | 1.1 | 1.2 | 1.2 | 0.8 | 0.8 | 1.0 | 1.2 | 1.1 | 1.0 |
| | Avg | 21.4 | 22.2 | 22.0 | 22.3 | 22.1 | 22.2 | 21.9 | 22.5 | 22.2 | 22.5 | 22.6 | 22.4 | 22.5 | 22.6 | 22.6 |

| Experiment | Needle | Pass Penetration [g] | | | | | | | | | | | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| B | 1 | 21 | 22 | 23 | 23 | 23 | 22 | 24 | 22 | 22 | 23 | 22 | 23 | 23 | 24 | 23 |
| | 2 | 23 | 24 | 23 | 24 | 24 | 23 | 23 | 24 | 25 | 26 | 26 | 27 | 28 | 29 | 29 |
| | 3 | 22 | 22 | 22 | 22 | 23 | 24 | 24 | 25 | 25 | 25 | 26 | 26 | 26 | 28 | 28 |
| | 4 | 26 | 25 | 24 | 24 | 24 | 24 | 25 | 26 | 25 | 25 | 25 | 26 | 26 | 25 | 26 |
| | 5 | 22 | 22 | 23 | 23 | 23 | 24 | 23 | 22 | 23 | 23 | 23 | 22 | 23 | 25 | 23 |
| | 6 | 23 | 23 | 23 | 23 | 23 | 22 | 24 | 23 | 24 | 24 | 23 | 25 | 24 | 24 | 24 |
| | 7 | 23 | 22 | 23 | 23 | 23 | 24 | 23 | 23 | 23 | 25 | 24 | 23 | 25 | 25 | 24 |
| | 8 | 22 | 23 | 23 | 24 | 24 | 24 | 24 | 24 | 24 | 24 | 23 | 27 | 25 | 25 | 25 |
| | 9 | 24 | 24 | 25 | 24 | 24 | 24 | 24 | 24 | 25 | 25 | 25 | 25 | 26 | 26 | 26 |
| | 10 | 22 | 22 | 21 | 22 | 22 | 22 | 22 | 22 | 23 | 22 | 23 | 23 | 24 | 24 | 23 |
| | St Dev | 1.4 | 1.1 | 1.1 | 0.8 | 0.7 | 0.9 | 0.8 | 1.4 | 1.1 | 1.2 | 1.4 | 1.8 | 1.6 | 1.7 | 2.1 |
| | Avg | 22.8 | 22.9 | 23.0 | 23.2 | 23.3 | 23.3 | 23.6 | 23.5 | 23.9 | 24.2 | 24.0 | 24.7 | 25.0 | 25.5 | 25.1 |

FIG. 7 is a graphical representation of the averaged results of Tests A and B in direct comparison. The y-axis shows the penetration force in grams needed to pass a needle through the penetration membrane. The x-axis shows the number of passes. The thick solid line represents the needles with conventional dip coating, as set forth in Test A, while the thin solid line represents the needles with the spray coating according to the present invention, as set forth in Test B.

As shown, the Test A needles initially required an average penetration force of about 29 g. The average penetration force for the Test A needles increased to 39 g after thirty passes. The Test B needles had an initial average penetration force of 21 g and an average penetration force of 25 g after thirty passes.

Exxon Isopar-K, 0.0022 g of Momentive®, catalyst in toluene, product no. SS8010, and 0.0127 of Momentive®, polymethyl hydrogen siloxane, product no. SS4300. Four test needles were each dipped into the base coating composition to coat their surfaces. The coated needles were then heated to 200 degrees Celsius in a convection oven furnace for one hour.

A top coat coating composition was prepared using 2.50 g of NuSil® MED4162 with 22.50 g of Exxon Isopar-K. The four needles were then each dipped into the top coating composition. The needles where then heated to 140 degrees Celsius in a convection oven and cured for three hours.

Once cured, the four needles were each passed through the penetration membrane thirty times and the penetration force in grams was recorded as shown in Table 5 below.

TABLE 5

| A Needle | Pass Penetration (g) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 | 61 | 71 | 78 | 84 | 88 | 95 | 97 | 101 | 100 | 104 | 108 | 110 | 110 | 109 | 110 |
| 2 | 65 | 67 | 70 | 73 | 76 | 79 | 82 | 83 | 84 | 84 | 86 | 90 | 90 | 90 | 90 |
| 3 | 60 | 69 | 75 | 80 | 85 | 88 | 92 | 94 | 95 | 98 | 99 | 100 | 102 | 102 | 103 |
| 4 | 62 | 65 | 69 | 73 | 76 | 79 | 82 | 84 | 86 | 88 | 89 | 92 | 92 | 94 | 95 |
| STDEV | 2 | 3 | 4 | 5 | 6 | 8 | 8 | 9 | 8 | 9 | 10 | 9 | 9 | 8 | 9 |
| AVG | 62 | 68 | 73 | 78 | 81 | 85 | 88 | 91 | 91 | 94 | 96 | 98 | 99 | 99 | 100 |

| A Needle | Pass Penetration (g) | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 1 | 111 | 111 | 112 | 110 | 112 | 114 | 112 | 113 | 113 | 112 | 116 | 114 | 113 | 111 | 112 |
| 2 | 92 | 93 | 95 | 95 | 96 | 96 | 98 | 99 | 102 | 102 | 104 | 104 | 104 | 107 | 109 |
| 3 | 101 | 101 | 104 | 107 | 104 | 103 | 104 | 104 | 103 | 105 | 107 | 107 | 105 | 108 | 108 |
| 4 | 95 | 95 | 97 | 124 | 121 | 122 | 125 | 123 | 127 | 127 | 129 | 130 | 133 | 136 | 132 |
| STDEV | 8 | 8 | 8 | 12 | 11 | 12 | 12 | 11 | 12 | 11 | 11 | 12 | 13 | 14 | 11 |
| AVG | 100 | 100 | 102 | 109 | 108 | 109 | 110 | 110 | 111 | 112 | 114 | 114 | 114 | 116 | 115 |

Test B

In Test B, five 0.026 inch diameter needles made from ETHALLOY® Alloy and having a taper cut point geometry were prepared for penetration testing. The needles were prepared by applying a base coating composition using swirl coating techniques. The base coating composition was made by combining 27.58 wt. % of the Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, poly-methyl hydrogen siloxane, product no. SS4300 was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator. The needles included in Test B were then batch cured at 140 degrees Celsius for three hours in a convection oven.

Once cured, the five needles were each passed through a Monmouth rubber synthetic media thirty times and the penetration force in grams was recorded as shown in Table 6 below.

TABLE 6

| B Needle | Pass Penetration (g) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 | 66 | 69 | 70 | 70 | 71 | 70 | 70 | 72 | 70 | 70 | 72 | 71 | 72 | 72 | 74 |
| 2 | 58 | 60 | 60 | 61 | 61 | 61 | 63 | 62 | 63 | 62 | 63 | 64 | 64 | 64 | 62 |
| 3 | 56 | 56 | 57 | 57 | 58 | 58 | 58 | 58 | 54 | 53 | 53 | 53 | 53 | 53 | 53 |
| 4 | 53 | 54 | 55 | 56 | 56 | 56 | 56 | 56 | 56 | 56 | 57 | 57 | 58 | 58 | 58 |
| 5 | 56 | 57 | 59 | 61 | 56 | 57 | 58 | 59 | 58 | 59 | 60 | 60 | 60 | 59 | 57 |
| STDEV | 4.9 | 5.9 | 5.8 | 5.5 | 6.3 | 5.7 | 5.7 | 6.3 | 6.4 | 6.5 | 7.2 | 6.9 | 7.1 | 7.2 | 8.0 |
| AVG | 58 | 59 | 60 | 61 | 60 | 60 | 61 | 61 | 60 | 60 | 61 | 61 | 61 | 61 | 61 |

| B Needle | Pass Penetration (g) | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 1 | 74 | 75 | 76 | 76 | 76 | 76 | 76 | 76 | 75 | 76 | 74 | 75 | 74 | 73 | 73 |
| 2 | 64 | 66 | 65 | 66 | 67 | 68 | 68 | 63 | 63 | 61 | 64 | 65 | 66 | 68 | 68 |
| 3 | 53 | 53 | 53 | 53 | 54 | 54 | 54 | 55 | 55 | 55 | 56 | 56 | 56 | 57 | 58 |
| 4 | 58 | 58 | 58 | 58 | 58 | 60 | 60 | 59 | 60 | 60 | 60 | 60 | 61 | 61 | 61 |
| 5 | 59 | 59 | 60 | 60 | 61 | 60 | 61 | 61 | 62 | 62 | 62 | 62 | 63 | 62 | 62 |
| STDEV | 8.0 | 8.5 | 8.7 | 8.8 | 8.6 | 8.5 | 8.4 | 7.9 | 7.4 | 7.9 | 6.7 | 7.2 | 6.7 | 6.3 | 6.0 |
| AVG | 62 | 62 | 62 | 63 | 63 | 64 | 64 | 63 | 63 | 63 | 63 | 64 | 64 | 64 | 64 |

Figure 8:
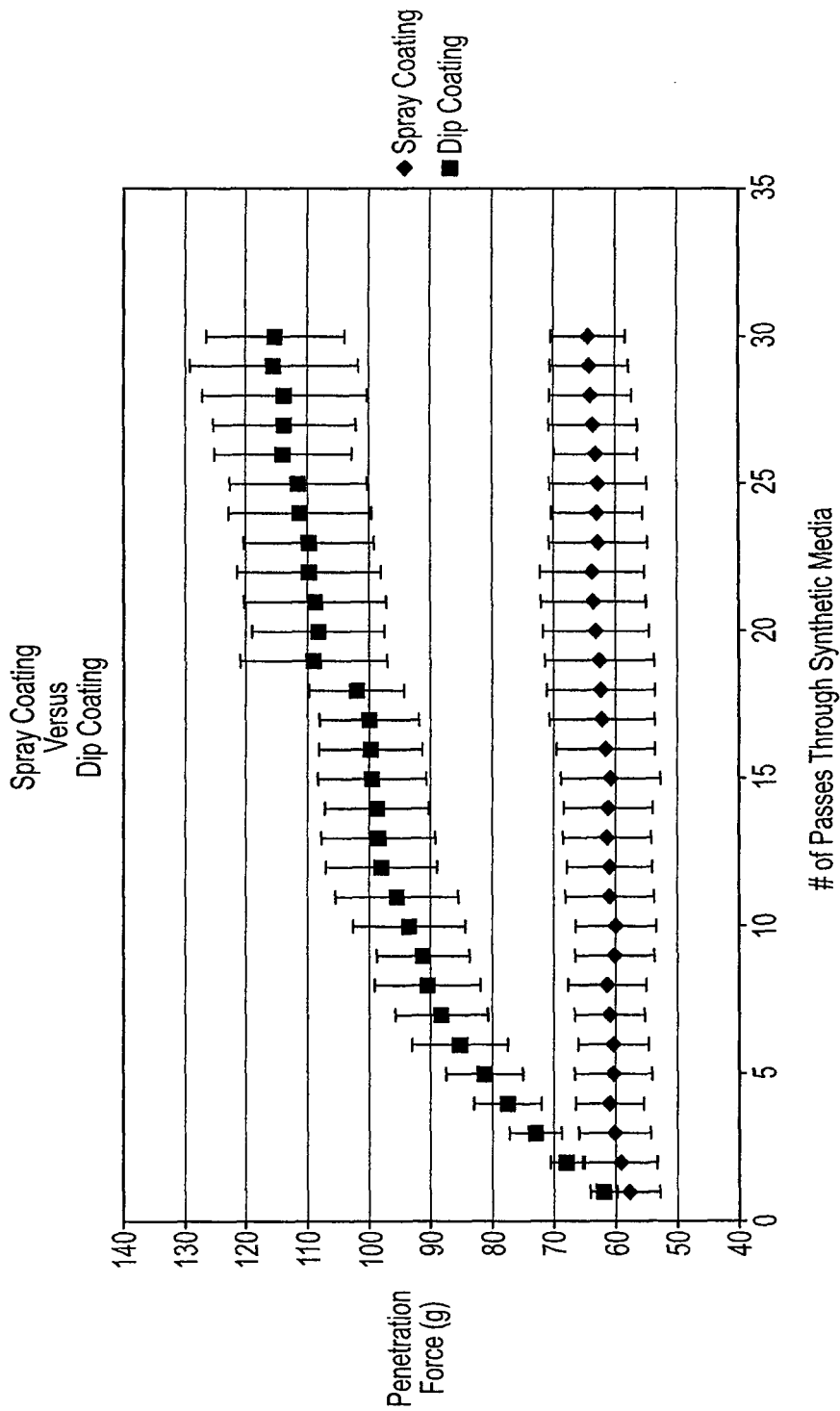
FIG. 8 is a graphical representation comparing the force required to pass surgical needles that are swirl coated through synthetic media versus surgical needles that are dip coated.

FIG. 8 is a graphical representation of the averaged results of Tests A and B in direct comparison. The y-axis shows the penetration force in grams needed to pass a needle through the penetration membrane. The x-axis shows the number of passes. The square points represent the needles with the dip coating, as set forth in Test A, while the diamond points represent the needles with the spray coating according to the present invention, as set forth in Test B.

As shown, the Test A needles with the dip coating initially required an average penetration force of 62 g. The average penetration force for the Test A needles increased to 115 g after thirty passes. The Test B needles with the spray coating performed with an initial average penetration force of 58 g and resulted in an average penetration force of 64 g after thirty passes. As can be seen, the needles in Test B with the spray coating required significantly less penetration force up to thirty passes.

Example 4

The penetration performance of various coating compositions and coating methods were tested. In the following Tests A, B, and C, three different types of needle coating compositions and application methods were examined. The penetration material for these tests was human cadaver carotid artery tissue.

Test A

In Test A, commercially available Ethicon BV-1 surgical needles having a 0.0105 inch diameter were tested. A coating was applied using the procedures associated with the manufacture of this series. In particular, a silicone dip was prepared using a concentration of NuSil® Product No. MED4162. The needles were placed on a moving carrier strip and dipped a first time. The needles were then flash cured in a hot box at approximately 190 degrees Celsius for twenty seconds. The needles were dipped a second time and flash cured again at the same settings as above. Finally, the needles were dipped a third time and then cured in a convection oven for 8 to 16 hours at 190 degrees Celsius.

Test B

In Test B, Ethicon tungsten-rhenium alloy needles having a 0.0105 inch diameter were tested. The needles were prepared by applying the Momentive® SS4044P primer coat at room temperature. A base coating composition was then applied over the primer using swirl coating techniques. The base coating composition was made by combining 27.58 wt. % of the Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, polymethyl hydrogen siloxane, product no. SS4300, was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator.

The needles included in Test B were then batch cured at 80 degrees Celsius for three hours in a convection oven. The needles were tested by passing each needle thirty times through the penetration membrane.

Test C

In Test C, a competing brand of commercially available surgical needles (0.010 inch diameter), typically used in similar procedures, was tested out of the package. The needles were tested by passing each needle thirty times through the penetration membrane.

FIG. 9 is a graphical representation of the averaged results of Tests A, B, and C in direct comparison. The y-axis shows the penetration force in grams needed to pass a needle through human cadaver tissue. The x-axis shows the number of passes. The triangular points represent the needles with the conventional dip coating, as set forth in Test A above. The circular points represent the needles prepared according to the present invention as forth in Test B above. The diamond points represent the competing brand of needles as set forth in Test C above.

As shown, the commercially available Test A needles having a dip coating initially required an average penetration force of about 16 g. The average penetration force for the Test A needles increased to about 18 g after thirty passes. The Test B needles with the coating according to the present invention performed with an initial average penetration force of about 13 g and maintained this penetration force after thirty passes. The competing brand of needles performed with an initial average penetration force of about 15 g and resulted in an average penetration force of about 25 g after thirty passes. As can be seen, the needles in Test B required significantly less penetration force up to thirty passes.

The use of two coatings as described above with respect to the present invention results in surgical needles that exhibit reduced tissue penetration force compared with standard surgical needles after an equivalent number of passes through tissue. Thus, both the lubricity of the needle as well as the durability of the coating is improved. This is believed to result for a number of reasons. For example, application of the base and top coats using a swirl coating process provides an even distribution of the coatings over the substrate. Furthermore, the composition of the coatings in combination with the methods of application and curing can result in significantly decreased average force required to repeatedly pass the needle through tissue. The curing time is also significantly decreased, resulting in more efficient manufacturing processes.

Example 6

The penetration performance of a medical device coated with a single, homogeneous coating was tested in comparison with the performance of a medical device coated with both top and base coatings. In the following Tests A, B, C, and D, two different types of needle coating compositions and application methods were examined. The needles were passed through Monmouth rubber synthetic media.

Tests A, B, and C

In Tests A, B, and C, ten commercially available Ethicon PS-2 surgical needles having a 0.024 inch diameter were tested. The ten test needles in each test were coated with a single, homogeneous coating. In Test A, the single, homogeneous coating was composed of a "Component A" mixture formed from 18.38 wt. % of the vinyl-functionalized organopolysiloxane, i.e., Momentive® Product Code No. MSC2631 silicone manufactured by Momentive® Performance Materials of Waterford, N.Y., 8.667 wt. % of the hydroxyl terminated polydimethylsiloxane, i.e., NuSil® Technologies Silicone Product No. MED4162 manufactured by NuSil® Technologies of Carpentaria, Calif., 72.85 wt. % of the HFE solvent, 0.0165 wt % of the catalyst, and 0.0936 wt. % of the crosslinker. The Component A mixture was equivalent to a 2:1 ratio of the base coating and top coating solutions and was mixed from master batches of the base and top coating solutions.

In Test B, the single, homogeneous coating was composed of a "Component B" mixture formed from 13.78 wt. % of the vinyl-functionalized organopolysiloxane, i.e., Momentive® Product Code No. MSC2631 silicone manufactured by Momentive® Performance Materials of Waterford, N.Y., 13.00 wt. % of the hydroxyl terminated polydimethylsiloxane, i.e., NuSil® Technologies Silicone Product No. MED4162 manufactured by NuSil® Technologies of Carpentaria, Calif., 73.13 wt. % of the HFE solvent, 0.0124 wt. % of the catalyst, and 0.0702 wt. % of the crosslinker. The Component B mixture was equivalent to a 1:1 ratio of the base coating and top coating solutions and was mixed from master batches of the base and top coating solutions.

In Test C, the single, homogeneous coating was composed of a "Component C" mixture formed from 9.189 wt. % of the vinyl-functionalized organopolysiloxane, i.e., Momentive® Product Code No. MSC2631 silicone manufactured by Momentive® Performance Materials of Waterford, N.Y., 17.33 wt. % of the hydroxyl terminated polydimethylsiloxane, i.e., NuSil® Technologies Silicone Product No. MED4162 manufactured by NuSil® Technologies of Carpentaria, Calif., 73.42 wt. % of the HFE solvent, 0.0083 wt. % of the catalyst, and 0.0468 wt. % of the crosslinker. The Component C mixture was equivalent to a 1:2 ratio of the base coating and top coating solutions and was mixed from master batches of the base and top coating solutions.

The ten test needles in each test were swirl coated with the single, homogeneous coating composition using a single pass spray using the SC-300 Swirl Coat™ Applicator and the Century® C-341 Conformal Coating System available from Asymtek® of Carlsbad, Calif. with the following parameters: 10 PSI fluid pressure, 50 PSI air assist, and a needle valve setting of 8. The coated needles were then heated to approximately 200 degrees Celsius in an infrared heater for about 20 seconds at ambient atmosphere.

As shown in Tables 7-9 below, the ten needles of each Tests A, B, and C were tested with thirty passes through the penetration membrane.

TABLE 7

| Experiment | Needle | Pass # Penetration (g) | | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Test A | 1 | 43 | 49 | 51 | 53 | 55 | 55 | 56 | 57 | 58 | 59 | 59 | 59 | 60 | 60 | 61 |
| | 2 | 40 | 45 | 47 | 49 | 50 | 52 | 53 | 54 | 55 | 56 | 57 | 57 | 58 | 59 | 59 |
| | 3 | 42 | 47 | 49 | 51 | 52 | 54 | 55 | 55 | 57 | 58 | 59 | 59 | 60 | 60 | 61 |
| | 4 | 42 | 46 | 48 | 51 | 52 | 54 | 56 | 57 | 58 | 59 | 60 | 61 | 61 | 62 | 63 |
| | 5 | 42 | 46 | 48 | 50 | 52 | 54 | 55 | 58 | 60 | 61 | 62 | 63 | 63 | 64 | 64 |
| | 6 | 42 | 46 | 49 | 51 | 53 | 54 | 54 | 55 | 57 | 58 | 58 | 60 | 60 | 60 | 61 |
| | 7 | 43 | 48 | 51 | 53 | 56 | 58 | 59 | 60 | 62 | 62 | 63 | 63 | 64 | 64 | 64 |
| | 8 | 40 | 45 | 48 | 49 | 50 | 52 | 53 | 54 | 55 | 56 | 57 | 57 | 58 | 58 | 58 |
| | 9 | 40 | 45 | 47 | 49 | 51 | 52 | 53 | 55 | 56 | 56 | 58 | 58 | 59 | 59 | 60 |
| | 10 | 39 | 42 | 45 | 47 | 48 | 49 | 50 | 51 | 52 | 53 | 54 | 54 | 55 | 56 | 57 |
| | Avg. | 41 | 46 | 48 | 50 | 52 | 53 | 54 | 56 | 57 | 58 | 59 | 59 | 60 | 60 | 61 |
| | St. Dev. | 1.4 | 1.9 | 1.8 | 1.9 | 2.4 | 2.4 | 2.4 | 2.5 | 2.8 | 2.7 | 2.6 | 2.8 | 2.6 | 2.5 | 2.4 |

| Experiment | Needle | Pass # Penetration (g) | | | | | | | | | | | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| Test A | 1 | 61 | 61 | 61 | 61 | 61 | 62 | 62 | 61 | 61 | 62 | 63 | 63 | 63 | 63 | 63 |
| | 2 | 60 | 60 | 61 | 62 | 63 | 63 | 63 | 64 | 64 | 64 | 64 | 65 | 65 | 66 | 66 |
| | 3 | 62 | 62 | 63 | 64 | 64 | 65 | 65 | 65 | 65 | 65 | 66 | 66 | 65 | 66 | 66 |
| | 4 | 66 | 64 | 64 | 64 | 64 | 65 | 66 | 65 | 66 | 66 | 66 | 66 | 66 | 66 | 67 |
| | 5 | 65 | 65 | 66 | 66 | 66 | 67 | 67 | 67 | 68 | 68 | 69 | 69 | 69 | 69 | 69 |
| | 6 | 62 | 62 | 63 | 63 | 63 | 63 | 64 | 65 | 65 | 65 | 66 | 66 | 66 | 67 | 68 |
| | 7 | 65 | 63 | 64 | 64 | 65 | 66 | 66 | 65 | 66 | 66 | 66 | 66 | 66 | 67 | 66 |
| | 8 | 59 | 59 | 59 | 59 | 59 | 60 | 60 | 61 | 61 | 61 | 61 | 61 | 61 | 62 | 61 |
| | 9 | 61 | 61 | 62 | 62 | 62 | 62 | 63 | 64 | 64 | 64 | 64 | 65 | 65 | 65 | 66 |
| | 10 | 57 | 57 | 58 | 58 | 59 | 59 | 60 | 61 | 60 | 61 | 61 | 62 | 62 | 62 | 62 |
| | Avg. | 62 | 61 | 62 | 62 | 63 | 63 | 64 | 64 | 64 | 64 | 65 | 65 | 65 | 65 | 65 |
| | St. Dev. | 2.9 | 2.4 | 2.4 | 2.5 | 2.4 | 2.6 | 2.5 | 2.1 | 2.6 | 2.3 | 2.5 | 2.3 | 2.3 | 2.3 | 2.6 |

TABLE 8

| Experiment | Needle | Pass # Penetration (g) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Test B | 1 | 52 | 59 | 61 | 63 | 65 | 67 | 68 | 68 | 70 | 71 | 71 | 72 | 73 | 73 | 74 |
| | 2 | 41 | 46 | 48 | 50 | 50 | 52 | 53 | 54 | 55 | 56 | 57 | 58 | 58 | 59 | 60 |
| | 3 | 40 | 44 | 47 | 49 | 50 | 52 | 53 | 54 | 55 | 56 | 57 | 58 | 58 | 59 | 60 |
| | 4 | 41 | 45 | 47 | 49 | 50 | 52 | 53 | 54 | 55 | 56 | 56 | 57 | 57 | 58 | 59 |
| | 5 | 37 | 41 | 44 | 45 | 47 | 48 | 49 | 50 | 51 | 52 | 52 | 52 | 53 | 54 | 54 |
| | 6 | 39 | 44 | 47 | 49 | 50 | 52 | 53 | 54 | 55 | 56 | 57 | 58 | 58 | 59 | 60 |
| | 7 | 45 | 49 | 51 | 52 | 54 | 54 | 55 | 56 | 56 | 57 | 57 | 58 | 59 | 59 | 59 |
| | 8 | 39 | 44 | 46 | 47 | 49 | 50 | 51 | 52 | 53 | 54 | 54 | 55 | 56 | 56 | 57 |
| | 9 | 40 | 44 | 46 | 47 | 48 | 50 | 52 | 52 | 54 | 54 | 55 | 56 | 57 | 57 | 58 |
| | 10 | 40 | 44 | 46 | 48 | 49 | 50 | 51 | 52 | 53 | 54 | 55 | 56 | 56 | 56 | 57 |
| | Avg. | 41 | 46 | 48 | 50 | 51 | 53 | 54 | 55 | 56 | 57 | 57 | 58 | 59 | 59 | 60 |
| | St. Dev. | 4.2 | 5.0 | 4.8 | 5.0 | 5.2 | 5.3 | 5.2 | 5.0 | 5.2 | 5.3 | 5.2 | 5.3 | 5.4 | 5.2 | 5.3 |

TABLE 8-continued

| | | Pass # Penetration (g) | | | | | | | | | | | | | | |
|---|---|---|---|---|---|---|---|---|---|---|---|---|---|---|---|---|
| Experiment | Needle | 16 | 17 | 18 | 19 | 20 | 21 | 22 | 23 | 24 | 25 | 26 | 27 | 28 | 29 | 30 |
| Test B | 1 | 74 | 74 | 75 | 76 | 75 | 76 | 77 | 77 | 78 | 78 | 78 | 79 | 79 | 79 | 80 |
| | 2 | 60 | 61 | 61 | 61 | 62 | 63 | 64 | 65 | 66 | 66 | 67 | 67 | 67 | 67 | 67 |
| | 3 | 60 | 60 | 61 | 62 | 62 | 64 | 63 | 63 | 64 | 64 | 64 | 64 | 64 | 65 | 64 |
| | 4 | 60 | 60 | 60 | 61 | 61 | 61 | 62 | 62 | 62 | 62 | 62 | 62 | 63 | 63 | 63 |
| | 5 | 55 | 55 | 56 | 56 | 57 | 57 | 57 | 58 | 58 | 58 | 59 | 58 | 58 | 59 | 59 |
| | 6 | 60 | 61 | 62 | 62 | 62 | 62 | 63 | 63 | 64 | 64 | 65 | 65 | 65 | 65 | 65 |
| | 7 | 60 | 60 | 60 | 60 | 60 | 61 | 61 | 62 | 62 | 62 | 62 | 63 | 62 | 63 | 63 |
| | 8 | 57 | 57 | 57 | 58 | 58 | 58 | 58 | 59 | 59 | 59 | 60 | 60 | 60 | 60 | 60 |
| | 9 | 59 | 60 | 60 | 60 | 61 | 61 | 61 | 61 | 62 | 62 | 62 | 62 | 62 | 62 | 63 |
| | 10 | 58 | 58 | 58 | 59 | 59 | 60 | 60 | 60 | 60 | 60 | 60 | 61 | 61 | 61 | 61 |
| | Avg. | 60 | 61 | 61 | 62 | 62 | 62 | 63 | 63 | 64 | 64 | 64 | 64 | 64 | 64 | 65 |
| | St. Dev. | 5.1 | 5.1 | 5.3 | 5.4 | 5.0 | 5.3 | 5.5 | 5.3 | 5.6 | 5.6 | 5.5 | 5.8 | 5.8 | 5.7 | 5.9 |

TABLE 9

| | | Pass # Penetration (g) | | | | | | | | | | | | | | |
|---|---|---|---|---|---|---|---|---|---|---|---|---|---|---|---|---|
| Experiment | Needle | 1 | 2 | 3 | 4 | 5 | 6 | 7 | 8 | 9 | 10 | 11 | 12 | 13 | 14 | 15 |
| Test C | 1 | 41 | 45 | 48 | 49 | 51 | 53 | 54 | 56 | 57 | 57 | 58 | 59 | 60 | 61 | 62 |
| | 2 | 41 | 46 | 49 | 51 | 53 | 55 | 56 | 58 | 60 | 60 | 61 | 62 | 63 | 63 | 64 |
| | 3 | 42 | 46 | 49 | 51 | 52 | 53 | 54 | 55 | 56 | 57 | 57 | 58 | 58 | 60 | 60 |
| | 4 | 39 | 43 | 46 | 48 | 50 | 51 | 52 | 53 | 55 | 56 | 56 | 57 | 57 | 58 | 60 |
| | 5 | 40 | 47 | 51 | 53 | 54 | 56 | 57 | 58 | 59 | 60 | 60 | 62 | 62 | 62 | 63 |
| | 6 | 39 | 43 | 46 | 48 | 50 | 52 | 54 | 55 | 56 | 57 | 57 | 58 | 59 | 59 | 59 |
| | 7 | 40 | 44 | 48 | 50 | 52 | 54 | 55 | 56 | 58 | 58 | 59 | 60 | 60 | 61 | 62 |
| | 8 | 40 | 45 | 48 | 50 | 52 | 54 | 56 | 58 | 59 | 60 | 61 | 62 | 63 | 63 | 64 |
| | 9 | 40 | 46 | 48 | 50 | 52 | 53 | 55 | 55 | 57 | 58 | 58 | 59 | 60 | 60 | 61 |
| | 10 | 39 | 45 | 48 | 50 | 52 | 53 | 55 | 56 | 56 | 57 | 58 | 58 | 59 | 59 | 60 |
| | Avg. | 40 | 45 | 48 | 50 | 52 | 53 | 55 | 56 | 57 | 58 | 59 | 60 | 60 | 61 | 62 |
| | St. Dev. | 1.0 | 1.3 | 1.4 | 1.5 | 1.2 | 1.4 | 1.4 | 1.6 | 1.6 | 1.5 | 1.7 | 1.9 | 1.9 | 1.5 | 1.7 |

| | | Pass # Penetration (g) | | | | | | | | | | | | | | |
|---|---|---|---|---|---|---|---|---|---|---|---|---|---|---|---|---|
| Experiment | Needle | 16 | 17 | 18 | 19 | 20 | 21 | 22 | 23 | 24 | 25 | 26 | 27 | 28 | 29 | 30 |
| Test C | 1 | 62 | 63 | 63 | 64 | 63 | 64 | 64 | 65 | 66 | 66 | 66 | 66 | 66 | 66 | 66 |
| | 2 | 64 | 66 | 69 | 70 | 70 | 70 | 71 | 71 | 71 | 71 | 71 | 71 | 71 | 72 | 72 |
| | 3 | 60 | 61 | 60 | 61 | 61 | 61 | 63 | 62 | 63 | 63 | 63 | 64 | 64 | 63 | 64 |
| | 4 | 63 | 63 | 63 | 64 | 64 | 65 | 65 | 65 | 65 | 65 | 65 | 64 | 65 | 65 | 66 |
| | 5 | 63 | 64 | 64 | 63 | 65 | 65 | 65 | 66 | 67 | 67 | 67 | 67 | 67 | 67 | 67 |
| | 6 | 60 | 60 | 60 | 61 | 61 | 62 | 62 | 62 | 62 | 65 | 66 | 67 | 68 | 68 | 68 |
| | 7 | 63 | 63 | 63 | 64 | 64 | 64 | 64 | 65 | 65 | 66 | 66 | 66 | 66 | 67 | 66 |
| | 8 | 64 | 66 | 66 | 66 | 66 | 66 | 66 | 66 | 67 | 67 | 67 | 67 | 68 | 68 | 68 |
| | 9 | 61 | 62 | 62 | 62 | 62 | 62 | 63 | 63 | 63 | 64 | 64 | 64 | 66 | 65 | 65 |
| | 10 | 60 | 61 | 62 | 63 | 62 | 63 | 64 | 64 | 64 | 65 | 65 | 65 | 65 | 65 | 66 |
| | Avg. | 62 | 63 | 63 | 64 | 64 | 64 | 65 | 65 | 65 | 66 | 66 | 66 | 67 | 67 | 67 |
| | St. Dev. | 1.6 | 2.0 | 2.7 | 2.7 | 2.7 | 2.6 | 2.5 | 2.6 | 2.6 | 2.2 | 2.2 | 2.1 | 2.0 | 2.5 | 2.2 |

Test D

In Test D, ten commercially available Ethicon PS-2 surgical needles having a 0.024 inch diameter were tested. The needles were prepared by applying a base coating composition using the swirl coating techniques and parameters described above in Tests A, B, and C. The base coating composition was made by combining 27.58 wt. % of Momentive®, vinyl functionalized base polymer, product no. MSC2631, with 72.25 wt. % of the HFE 72-DE solvent. Momentive® catalyst in toluene, product no. SS8010, was then added to the mixture at 0.02 wt. %, and Momentive® polymethyl hydrogen siloxane crosslinker, product no. SS4300 was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator.

The needles included in Test D were then batch cured at 140 degrees Celsius for three hours in a convection oven. The needles were tested by passing each needle thirty times through the penetration membrane. The force required to do so is set forth in Table 10.

TABLE 10

| Experiment | Needle | Pass # Penetration (g) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Test D | 1 | 46 | 50 | 51 | 53 | 54 | 55 | 55 | 56 | 57 | 58 | 58 | 58 | 58 | 58 | 58 |
| | 2 | 48 | 52 | 56 | 56 | 58 | 60 | 61 | 62 | 62 | 63 | 64 | 64 | 64 | 64 | 65 |
| | 3 | 47 | 50 | 52 | 53 | 54 | 56 | 56 | 57 | 58 | 58 | 58 | 58 | 58 | 59 | 60 |
| | 4 | 43 | 46 | 47 | 48 | 49 | 50 | 50 | 50 | 51 | 52 | 52 | 54 | 55 | 55 | 55 |
| | 5 | 45 | 48 | 49 | 50 | 50 | 52 | 52 | 53 | 53 | 54 | 54 | 55 | 55 | 55 | 55 |
| | 6 | 47 | 49 | 50 | 52 | 52 | 53 | 54 | 54 | 55 | 56 | 56 | 56 | 56 | 57 | 57 |
| | 7 | 46 | 49 | 50 | 51 | 52 | 52 | 53 | 53 | 52 | 53 | 53 | 54 | 54 | 55 | 56 | 56 |
| | 8 | 44 | 45 | 48 | 48 | 49 | 50 | 50 | 50 | 50 | 51 | 51 | 52 | 53 | 53 | 54 |
| | 9 | 45 | 48 | 48 | 51 | 52 | 53 | 54 | 54 | 55 | 55 | 56 | 57 | 57 | 57 | 58 |
| | 10 | 44 | 47 | 48 | 49 | 49 | 50 | 51 | 51 | 51 | 51 | 52 | 52 | 52 | 52 | 53 |
| | Avg. | 46 | 48 | 50 | 51 | 52 | 53 | 54 | 54 | 54 | 55 | 56 | 56 | 56 | 57 | 57 |
| | St. Dev. | 1.6 | 2.1 | 2.6 | 2.5 | 2.9 | 3.2 | 3.3 | 3.7 | 3.8 | 3.8 | 3.9 | 3.6 | 3.3 | 3.4 | 3.5 |

| Experiment | Needle | Pass # Penetration (g) | | | | | | | | | | | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| Test D | 1 | 59 | 60 | 60 | 61 | 60 | 61 | 62 | 62 | 62 | 64 | 64 | 65 | 66 | 66 | 66 |
| | 2 | 66 | 66 | 67 | 67 | 67 | 68 | 67 | 67 | 68 | 68 | 69 | 68 | 68 | 69 | 69 |
| | 3 | 60 | 60 | 60 | 61 | 61 | 62 | 62 | 62 | 61 | 62 | 62 | 62 | 62 | 62 | 63 |
| | 4 | 55 | 56 | 56 | 56 | 57 | 57 | 58 | 58 | 58 | 58 | 58 | 59 | 59 | 59 | 59 |
| | 5 | 56 | 56 | 58 | 58 | 59 | 59 | 60 | 60 | 60 | 60 | 60 | 61 | 61 | 62 | 61 |
| | 6 | 58 | 59 | 59 | 59 | 59 | 60 | 60 | 60 | 60 | 60 | 60 | 61 | 60 | 60 | 60 |
| | 7 | 56 | 56 | 57 | 58 | 58 | 57 | 58 | 58 | 58 | 59 | 59 | 59 | 59 | 59 | 60 |
| | 8 | 54 | 55 | 54 | 54 | 54 | 55 | 55 | 55 | 56 | 56 | 56 | 56 | 56 | 57 | 57 |
| | 9 | 58 | 58 | 59 | 59 | 59 | 59 | 60 | 60 | 62 | 60 | 60 | 61 | 61 | 62 | 62 |
| | 10 | 53 | 53 | 54 | 54 | 54 | 54 | 55 | 55 | 55 | 55 | 55 | 55 | 55 | 55 | 56 |
| | Avg. | 58 | 58 | 58 | 59 | 59 | 59 | 60 | 60 | 60 | 60 | 60 | 61 | 61 | 61 | 61 |
| | St. Dev. | 3.7 | 3.6 | 3.7 | 3.8 | 3.7 | 4.0 | 3.6 | 3.6 | 3.7 | 3.8 | 4.0 | 3.9 | 4.0 | 4.1 | 3.9 |

FIG. 10 is a graphical representation of the averaged results of Tests A, B, C, and D in direct comparison. The y-axis shows the penetration force in grams needed to pass a needle through the penetration membrane. The x-axis shows the number of passes.

As can be seen, the needles that were coated with a single, homogeneous coating had an initial penetration force of about 41 g in Tests A and B and about 40 g in Test C. The penetration force increased somewhat over the thirty passes, and the needles required an average maximum force of about 65 g in Tests A and B and about 67 g in Test C after thirty passes. In contrast, the needles that were coated with the two coats, i.e., the base coating and the top coating, had an initial penetration force of about 46 g. The average maximum penetration force after thirty passes was about 61 g. As shown, the needles that were coated with a single, homogeneous coat initially required about 5 g to 6 g less force on average than the needles that were coated with two layers.

The use of a single, homogeneous coating as described above with respect to the present invention results in surgical needles that exhibit reduced initial tissue penetration force compared with both surgical needles having two coats and with standard surgical needles after an equivalent number of passes through tissue. Thus, both the lubricity of the needle as well as the durability of the coating is improved. This is believed to result for a number of reasons. For example, application of the single, homogeneous coating using a swirl coating process provides an even and thin distribution of the coating over the substrate. Furthermore, the composition of the coating in combination with the methods of application and curing can result in significantly decreased average force required to repeatedly pass the needle through tissue. The curing time is also significantly decreased compared to the cure time required when two coatings, such as the top coating and the base coating, are used, resulting in more efficient manufacturing processes.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for coating a medical device, comprising:
   spray coating a refractory alloy surface of a surgical needle having a tissue penetrating tip with a primer comprising silicon to create a primed surface of the surgical needle; and
   applying, as a liquid spray, a base coating to at least a portion of the primed surface of the surgical needle, wherein the base coating is different from the primer and comprises a vinyl functionalized organopolysiloxane and a hydrofluoroether solvent; and
   applying, as a liquid spray, a top coating over the base coating, wherein the top coating is different from the primer and the base coating and comprises a polydimethylsiloxane and a hydrofluoroether solvent.

2. The method of claim 1, wherein the primer is applied as a liquid spray.

3. The method of claim 2, wherein applying the primer as a liquid spray comprises swirl coating.

4. The method of claim 1, wherein the surgical needle is formed from a tungsten-rhenium alloy.

5. The method of claim 1, further comprising curing the top coating applied over the base coating for a time in the range of about 10 seconds to about 30 seconds.

6. The method of claim 1, further comprising curing the top coating applied over the base coating for a time in the range of about 1 second to about 60 seconds.

7. The method of claim 6, wherein at least one of the base and top coating further comprises a solvent having a boiling point less than about 43 degrees Celsius.

8. The method of claim 1, wherein applying at least one of the primer, the base coating, and the top coating as a liquid spray comprises swirl coating.

9. A method for coating a medical device, comprising:
spray coating a metal surface of a surgical needle comprising a tissue penetrating tip with a primer coating;
spray coating the primed surface of the surgical needle with a base coating that is different from the primer coating and comprises a vinyl functionalized organopolysiloxane and hydrofluoroether; and
spray coating the base coating with a top coating that is different from the primer and base coatings and comprises a polydimethylsiloxane and hydrofluoroether; and
curing the top coating after the spray coating of the top coating.

10. The method of claim 9, wherein the spray coating comprises swirl coating.

* * * * *